(12) United States Patent
Adamson et al.

(10) Patent No.: US 8,840,877 B2
(45) Date of Patent: Sep. 23, 2014

(54) POLYSACCHARIDE-PROTEIN CONJUGATES REVERSIBLY COUPLED VIA IMINE BONDS

(75) Inventors: Gord Adamson, Mississauga (CA); David Bell, Mississauga (CA); Steven Brookes, Mississauga (CA)

(73) Assignee: Therapure Biopharma Inc., Mississauga, Ontario (CA)

( * ) Notice: Subject to any disclaimer, the term of this patent is extended or adjusted under 35 U.S.C. 154(b) by 49 days.

(21) Appl. No.: 12/999,076

(22) PCT Filed: Jun. 26, 2009

(86) PCT No.: PCT/CA2009/000885
§ 371 (c)(1),
(2), (4) Date: Dec. 15, 2010

(87) PCT Pub. No.: WO2009/155705
PCT Pub. Date: Dec. 30, 2009

(65) Prior Publication Data
US 2011/0104114 A1 May 5, 2011

(30) Foreign Application Priority Data

Jun. 26, 2008 (GB) .................................. 0811743.4

(51) Int. Cl.
| | | |
|---|---|---|
| *A61K 38/17* | (2006.01) | |
| *A61K 38/18* | (2006.01) | |
| *A61K 38/19* | (2006.01) | |
| *A61K 38/22* | (2006.01) | |
| *A61K 38/36* | (2006.01) | |
| *A61K 38/38* | (2006.01) | |
| *A61K 38/43* | (2006.01) | |
| *A61K 38/55* | (2006.01) | |
| *A61K 39/395* | (2006.01) | |
| *A61K 47/48* | (2006.01) | |
| *A61K 38/44* | (2006.01) | |
| *A61K 38/57* | (2006.01) | |
| *C07K 16/28* | (2006.01) | |
| *A61K 38/16* | (2006.01) | |
| *A61K 38/50* | (2006.01) | |
| *A61K 38/28* | (2006.01) | |
| *A61K 38/21* | (2006.01) | |
| *A61K 38/37* | (2006.01) | |
| *A61K 49/00* | (2006.01) | |

(52) U.S. Cl.
CPC ....... *A61K 47/4823* (2013.01); *A61K 47/48215* (2013.01); *A61K 38/385* (2013.01); *A61K 38/193* (2013.01); *A61K 38/44* (2013.01); *C12Y 305/01001* (2013.01); *A61K 38/57* (2013.01); *C07K 16/2896* (2013.01); *A61K 38/166* (2013.01); *A61K 38/50* (2013.01); *A61K 38/28* (2013.01); *A61K 38/212* (2013.01); *A61K 38/37* (2013.01); *A61K 49/0017* (2013.01); *C12Y 107/03003* (2013.01)
USPC ....... 424/85.1; 424/85.4; 424/94.4; 424/94.5; 424/94.6; 424/178.1; 424/198.1; 514/5.9; 514/9.7; 514/14.1; 514/20.1

(58) Field of Classification Search
None
See application file for complete search history.

(56) References Cited

U.S. PATENT DOCUMENTS

| | | | |
|---|---|---|---|
| 6,011,008 A | 1/2000 | Domb et al. | |
| 6,956,119 B2 | 10/2005 | Loibner et al. | |
| 7,816,516 B2 * | 10/2010 | Sommermeyer et al. | ..... 536/124 |

FOREIGN PATENT DOCUMENTS

| | | |
|---|---|---|
| CA | 1158159 | 12/1983 |
| CA | 2326715 | 10/1999 |
| CA | 2558725 | 10/2005 |
| CA | 2558738 | 10/2005 |

OTHER PUBLICATIONS

Singh et al., "An insulin delivery system from oxidized cellulose", Journal of Biomedical Research (1981), 15:655-661.
Balakrishnan et al. "Self-cross-linking biopolymers as injectable in situ forming biodegradable scaffolds" Biomaterials (2005), 26:3941-3951.
Ikada et al. "Grafting of proteins onto polymer surfaces with the use of oxidized starch" Journal of Biomedical Materials Research (1979) 13:607-622.

* cited by examiner

*Primary Examiner* — Ruixiang Li
(74) *Attorney, Agent, or Firm* — Nixon & Vanderhye, P.C.

(57) ABSTRACT

Method for preparing an oxidized polysaccharide-protein composition, by (a) oxidizing a polysaccharide with an oxidizing agent to form an oxidized polysaccharide where less than 20% of the oxidized units are comprised of alpha-hydroxy aldehyde units, (b) reacting the oxidized polysaccharide with a protein to form a composition comprising an oxidized polysaccharide-protein conjugate, and (c) maintaining the oxidized polysaccharide-protein conjugate composition by placing it in an environment where the temperature is less than 8° C. The oxidized polysaccharide and the protein are conjugated via one or more imine bonds, the oxidized polysaccharide-protein composition is soluble in aqueous solvent, and the composition is capable of releasing the protein.

24 Claims, 18 Drawing Sheets

POLYSACCHARIDE-PROTEIN CONJUGATES REVERSIBLY COUPLED VIA IMINE BONDS

FIELD OF THE INVENTION

The present invention relates to methods for preparing oxidised polysaccharide-protein conjugates, compositions comprising such conjugates, and uses thereof. Conjugates prepared by the method result in increased half-life and sustained activity of the protein in vitro and in vivo for therapeutic and diagnostic purposes. Compositions prepared as described have improved bioactivity compared to protein that has not been so prepared.

BACKGROUND OF THE INVENTION

Many therapeutic proteins and other drugs have been found to have a short half-life in circulation and short-lived bioavailability. The half-life is dictated by specific and non-specific clearance mechanisms and the rate of degradation of the protein or drug. As a consequence of this short-lived bioavailability, high initial doses and frequent dosing regimens may be required to sustain therapeutic levels of drug, potentially resulting in dose-related toxicities, poor patient compliance and increased treatment cost. Methods are required that will increase protein and drug half-life while sustaining protein activity. An ideal method for this purpose would increase protein half-life by attachment to a readily available biocompatible polymer using a simple and scaleable process.

Attachment (e.g., conjugation) of drugs and proteins to macromolecular carriers is a known means of increasing drug and protein half-life. The current known conjugation methods concentrate on reactions that form an irreversible attachment between the macromolecular carrier and the drug or protein. One example of such bioconjugation is the attachment of proteins to the non-natural carrier, polyethylene glycol (PEG), a process termed PEGylation. PEGs are synthetic polymer strands that can be chemically activated for attachment to proteins, usually through a single point of attachment of the PEG molecule to the protein, to increase the size of the protein. A variety of PEGylated protein conjugates have been disclosed, for example, in U.S. Pat. No. 4,002,531, U.S. Pat. No. 5,122,614 and U.S. Pat. No. 5,824,784. Conjugates such as PEG-interferon have been approved for use in the treatment of hepatitis C virus infection and demonstrate a longer half-life and lower dosing frequency compare to unmodified interferon (IFN). Other PEGylated proteins, including PEGylated versions of G-CSF, blood clotting factors, enzymes and other high value therapeutic proteins, are currently in clinical use or under development. One key drawback is that often PEGylated proteins only sustain a fraction of the activity of the native protein since the PEG is attached directly to, or is located near to, sites on the protein that are required for activity. For example, PEGylated interferon-$\alpha_{2a}$ (Roche's Pegasys® and PEGylated interferon-$\alpha_{2b}$ (Schering's Pegintron®), which are approved drugs, have only 6% and 28% of the activity of their corresponding unmodified interferons, respectively, and PEGylated asparaginase (Enzon's Oncaspar®), an approved anti-cancer treatment, has only 50% of the activity of unmodified asparaginase. Furthermore, PEGylation methods result in irreversible attachment of the PEG to the protein, such that the protein is permanently modified in its lower activity PEG-protein form, and is not released in a more active form. As such, PEGylation requires careful selection of the protein drug modification site to minimize loss of activity.

Other ways to increase drug half-life include the production of fusion proteins (e.g., albumin-IFN) or the addition of new glycosylation sites to proteins (e.g., glycosylated erythropoietin) through genetic manipulation, as well as, chemical modification to cross-link, stabilize and polymerize proteins (e.g., o-raffinose- or glutaraldehyde-polymerized hemoglobin). Each of these approaches requires careful selection of the site of modification to minimize loss of protein activity.

Polysaccharide modification of proteins has also been used to increase the half-life of proteins. Polysaccharides are naturally occurring macromolecules that may be more biocompatible than synthetic polymers used for protein conjugation. In a typical polysaccharide conjugation process, vicinal diols of the polysaccharide are oxidized to form aldehydes that can react with amines on the protein by a reductive amination process to form stable secondary amine linkages. The oxidised polysaccharide initially reacts with the protein to produce an imine intermediate that is reduced under the reaction conditions to a stable secondary amine linkage. Typical reducing agents used to carry out the reductive amination process include sodium cyanoborohydride, sodium borohydride and dimethylamino borane, among others. For example, U.S. Pat. No. 4,356,170 discloses covalently linking a protein to an oxidised antigenic polysaccharide via an amine linkage formed by reductive amination to form a stable conjugate. The formation of a stable conjugate that does not dissociate under physiological conditions is important because the authors report an oxidised polysaccharide-tetanus toxoid conjugate that showed enhanced immunological properties compared to the initial polysaccharide antigen. US 2005/0063943 discloses a conjugate of hydroxyalkyl starch covalently bonded to an active agent (such as a protein) via an amine linkage formed by reductive amination. US 2005/0063943 also discloses using a linker to indirectly connect the hydroxyalkyl starch to an active agent via reductive amination. US 2007/0134197 discloses conjugates of hydroxyalkyl starch and a protein formed by reductive amination. Conjugation was through single point attachment between the hydroxyalkyl starch and the protein. Under the disclosed reductive amination conditions the hydroxyalkyl starch and the protein inevitably produce a secondary amine product. The importance of using reducing conditions was demonstrated by a control reaction between an aldehydo-hydroxyethyl starch and erythropoietin (EPO), which failed to produce any conjugate in the absence of reducing agents. U.S. Pat. No. 5,177,059 discloses conjugating polymyxin B to dextran via either a carbamate linkage or an amine linkage via reductive amination. In each of these cases, reductive amination is used to form conjugates of proteins with oxidised polysaccharide. However, such amine linkages are not reversible (i.e., the bond between the oxidised polysaccharide and the protein is not dissociated by processes such as non-enzymatic hydrolysis or transimination under physiologic conditions).

Proteins have also been conjugated to oxidized polysaccharides without reduction to form imine-linked conjugates. U.S. Pat. No. 5,554,730 discloses a method of preparing a stable immunogenic polysaccharide-protein conjugate microparticle. This method oxidises a polysaccharide and then combines it with a protein to form a Schiff base conjugate. This method requires the presence of a macromolecular crowding agent in order to form the conjugate microparticle. The polysaccharide is chosen from bacterial antigens capable of inducing an immune response when coupled to a protein. Hence, in order to produce the desired immune response, it is important to select components that form a conjugate that does not readily dissociate under physiologic conditions.

Indeed, in the sole example an immunogenic capsular polysaccharide derived from bacteria is conjugated to a protein, tetanus toxoid that is also immunogenic. U.S. Pat. No. 6,011,008 discloses conjugates prepared by oxidising polysaccharides such as dextran or arabinogalactan to a dialdehyde and reacting with a low molecular weight drug or polypeptide to form a Schiff base conjugate. This method aims to provide a stable water soluble conjugate whose biological activity is comparable to the activity of the free substance. Hence, components were chosen that do not readily dissociate once a conjugate is formed. The degree of oxidation in the dialdehyde varied from 5 to 50%. Dextran and arabinogalactan contain large numbers of 1,2,3-triol monomer units that upon oxidation form alpha-hydroxy aldehydes that can form irreversible linkages to polypeptides in the absence of reduction. Such irreversible linkages are formed by an Amadori rearrangement. These irreversible linkages limit the release or dissociation of the protein from the conjugate. Protein release was less than 30% in all examples of non-reduced conjugates in U.S. Pat. No. 6,011,008. U.S. Pat. No. 6,956,119 discloses conjugates prepared by partially oxidising polysaccharides such as dextran or mannan and reacting them with an antigenic polypeptide. In particular, U.S. Pat. No. 6,956,119 teaches selecting mannan as the polysaccharide so that the corresponding conjugate is taken up by cells that carry the mannose receptor. Both dextran and mannan contain 1,2,3-triol monomer units that upon oxidation form alpha-hydroxy aldehydes that can form irreversible linkages to polypeptides.

All of the current methods to modify proteins to increase half-life have limitations that may be addressed by alternative protein modification strategies. The ideal composition of a polymer-protein conjugate for increased protein half-life and sustained activity is one in which the majority of the polymer-protein linkages are reversible. Such linkages between the polymer and the protein are dissociated by processes such as non-enzymatic hydrolysis, cleavage or transimination under physiological conditions. Such conjugates avoid the problems of decreased activity observed with many known conjugates. Thus, there is a need for conjugates that reversibly attach a protein to a carrier enabling increased protein half-life and allow for release of the protein in an active form to provide sustained activity.

The inventors have discovered an efficient and widely applicable method to prepare compositions of reversible polysaccharide-protein conjugates and increase protein half-life and sustain activity. The method does not require modification site selection as necessary for many of the previously reported methods. Compositions are prepared using polysaccharides, such as those with low 1,2,3-triol contents, that do not form significant amounts of alpha-hydroxy aldehydes upon oxidation in order to minimize the formation of irreversible linkages in the absence of reduction. Proteins are readily reacted with the oxidized polysaccharide to produce conjugates with optimal product size and protein load, improved stability and sustained bioactivity. Through appropriate selection of polysaccharide-protein reaction conditions, the stability of the conjugate can be adjusted to provide the desired protein release profile.

In one aspect the present invention provides a method of preparing a composition comprising an oxidised polysaccharide-protein comprising the steps of:
  (a) oxidising a polysaccharide with an oxidising agent to form an oxidised polysaccharide; and
  (b) reacting the oxidised polysaccharide with a protein to form a composition comprising an oxidised polysaccharide-protein conjugate wherein the oxidised polysaccharide and the protein are conjugated via one or more imine bonds; and wherein the oxidised polysaccharide comprises essentially no alpha-hydroxy aldehyde units.

In another aspect, the present invention provides an oxidised polysaccharide-protein composition comprising an oxidised polysaccharide and a protein; wherein the oxidised polysaccharide comprises essentially no alpha-hydroxy aldehyde units and wherein the protein is conjugated to the oxidised polysaccharide via one or more imine bonds.

In another aspect the present invention provides an oxidised polysaccharide-protein composition obtained by a method as described herein.

In another aspect the present invention provides an oxidised polysaccharide-protein composition for use in the treatment or diagnosis of a disease or condition wherein the composition comprises an oxidised polysaccharide and a protein; wherein the oxidised polysaccharide comprises essentially no alpha-hydroxy aldehyde units and wherein the protein is conjugated to the oxidised polysaccharide via one or more imine bonds; and wherein the disease or condition is selected from hormone deficiency, hemostasis, thrombosis, metabolic enzyme deficiency, pulmonary disorder, gastrointestinal disorder, immunodeficiency, hematopoiesis, fertility disorders, immunoregulation, endocrine disorders, hemophilia, shock, growth regulation, cancer, transplantation, infectious disease, inflammation and detoxification.

In another aspect, the present invention provides an oxidised polysaccharide-protein composition wherein the protein is conjugated to the oxidised polysaccharide via one or more imine bonds.

The polysaccharide-protein compositions, their preparation processes and uses as described herein offer several advantages over those of previously disclosed protein conjugates. Previous conjugates prepared by linkage of a protein to polymers such as PEG and polysaccharide have decreased protein activity as a result of irreversible modification of sites on the protein essential for activity. Such conjugates had reduced protein activity upon analysis or following administration. Attempts to limit this decrease in activity require site-specific chemistry methods and careful selection of specific polymer attachment sites on the protein. Therefore, in the field of therapeutic protein conjugate compositions intended to increase half-life and duration of activity in vivo, there is a need for conjugates of polysaccharide and protein with the ability to regain activity or to increase activity following administration, by minimizing the number of irreversible linkages between the polysaccharide and the protein.

The compositions described herein comprise a soluble mixture of a protein and a polysaccharide, wherein the composition allows for the sustained release of protein in the circulation with all the added benefits of such a sustained release technology. The composition preferably comprises a combination of a protein and a polysaccharide wherein the composition is capable of releasing the protein in an active form. Protein activity may be initially decreased as a result of linkage to the polysaccharide, and lost activity may be partially or totally regained upon release from the linked polysaccharide-protein conjugate form. In this way, the total protein specific activity may increase following administration. The linked polysaccharide-protein conjugate is comprised of oxidized polysaccharide molecules covalently linked to protein molecules via linkages that permit release of the protein from the polysaccharide component. The linkages are imine bonds (also known as or Schiff bases or azomethines), which can be released or dissociated by non-enzymatic hydrolysis or transimination via peptides, amino acids, proteins or other endogenous amines in plasma. The linkages are formed between aldehyde groups on the oxidized polysaccharide and amino groups on the protein by condensing under selected conditions. These linkages preferably account for all or the majority of linkages in the composition.

Compositions comprising the conjugate are preferably adjusted to a pH, ionic strength and concentration to maintain the majority of the total protein in the linked polysaccharide-protein conjugate form prior to administration to an animal or use under conditions requiring the release of the protein from the composition.

Properties of the conjugate were found to be controlled though selection of reaction parameters including the degree of polysaccharide oxidation, the size and polydispersity of the polysaccharide, the degree of hydroxyethylation, the ratio of oxidized polysaccharide to protein, the concentration of the protein, as well as reaction pH, temperature and time. These reaction conditions have been found to affect properties of the conjugate or of compositions comprising the conjugate. Selection of reaction parameters is used to control properties of the composition including the amount of protein conjugated to the polysaccharide, the rate of release of protein, the activity of the modified protein in the composition, the time-activity profile of the protein in solutions containing the composition, circulatory half-life of the protein and its in vivo biodistribution and activity, as well as the stability, solubility, and immunogenicity of the protein.

Composition

Preferably the oxidised polysaccharide-protein composition is obtained by a method as described herein.

In some aspects, the composition may further comprise a non-conjugated protein.

In another aspect, the present invention provides a composition comprising:
(i) an oxidised polysaccharide-protein conjugate as described herein; and
(ii) non-conjugated protein;
wherein the non-conjugated protein (ii) provides initial activity and the conjugated protein (i) provides sustained activity.

In another aspect, the present invention provides a method of providing enhanced activity of a protein in a patient comprising the step of administering to a subject a composition as described herein.

In another aspect, the present invention provides a method of providing enhanced activity of a protein in a patient comprising the step of administering to a subject a composition comprising:
(i) an oxidised polysaccharide-protein conjugate as described herein; and
(ii) non-conjugated protein
wherein the non-conjugated protein (ii) provides initial activity and the conjugated protein (i) provides sustained activity.

In another aspect, the present invention provides a composition comprising:
(i) an oxidised polysaccharide-protein conjugate as described herein; and
(ii) non-conjugated protein;
for the treatment of a disease,
wherein following administration of the composition the non-conjugated protein (ii) provides initial activity and the conjugated protein (i) provides sustained activity.

Preferably, the conjugated protein (i) enhances the circulatory half-life ($t_{1/2}$) relative to the circulatory half-life of non-conjugated protein.

Thus, depending on the level of purification applied or duration of reaction, the composition can contain a fraction of the total protein content in non-conjugated (i.e. in non-bound or free) form, either by addition of the protein, or in the form of unreacted protein residual from the reaction of the oxidised polysaccharide with the protein or in the form of non-conjugated (or free) protein in equilibrium with reversibly bound form in the conjugate. A fraction of free protein in the composition may provide immediate activity upon administration of the composition, and may also exist in equilibrium with the reversibly bound form of protein to maintain a fraction of the total protein in bound form.

The composition may also comprise an excipient suitable for administration to a human or an animal. Such excipients could include amino acids or other proteins.

Suitably the ratio and concentration of non-conjugated protein to polysaccharide-conjugated protein in the composition are controlled to maintain a substantial proportion of the protein in the conjugated form. Preferably the proportion of the protein in the conjugated form is greater than or equal to 50%; preferably, greater than or equal to 60%; preferably greater than or equal to 70%; preferably greater than or equal to 80%; preferably greater than or equal to 90%.

The concentration of total protein in the composition may be adjusted to maintain an equilibrium ratio of non-conjugated protein to polysaccharide-bound protein of less than 0.5:1; preferably less than 0.4:1; preferably less than 0.3:1; preferably less than 0.2:1; preferably less than 0.1:1.

Preferably, the composition is a liquid formulation.

Preferably, the composition is soluble; preferably soluble in aqueous solvent; preferably soluble at physiological pH; preferably soluble in the absence of glycol, polyvinylpyrrolidone and/or macromolecular crowding agents.

Preferably, the oxidised polysaccharide-protein composition further comprises at least one further protein and each protein is conjugated to the oxidised polysaccharide via one or more imine bonds. Preferably there is one further protein. Suitably, the protein is streptokinase and the further protein is albumin.

Conjugate

In a further aspect, there is provided a method of preparing an oxidised polysaccharide-protein conjugate comprising the steps of:
(a) oxidising a polysaccharide with an oxidising agent to form an oxidised polysaccharide; and
(b) reacting the oxidised polysaccharide with a protein to form a conjugate wherein the oxidised polysaccharide and the protein are conjugated via one or more imine bonds; and wherein the oxidised polysaccharide comprises essentially no alpha-hydroxy aldehyde units; and optionally
(c) lowering the pH of the oxidised polysaccharide-protein conjugate to a pH of from 5 to 6 for formulation purposes.

In a further aspect, there is provided an oxidised polysaccharide-protein conjugate prepared by a method as described herein.

In a further aspect, there is provided an oxidised polysaccharide-protein conjugate as described herein for the treatment or diagnosis of a disease or condition wherein the conjugate comprises a protein conjugated to the oxidised polysaccharide via one or more imine bonds.

Preferably the oxidised polysaccharide-protein conjugate is soluble; preferably soluble in aqueous solvent; preferably soluble at physiological pH; preferably soluble in the absence of glycol, polyvinylpyrrolidone and/or macromolecular crowding agents.

Preferably the oxidised polysaccharide-protein conjugate is less than 0.1 μm in size; preferably less than 0.09 μm; preferably less than 0.08 μm; preferably less than 0.07 μm.

Preferably the oxidised polysaccharide and the protein are conjugated via two or more imine bonds.

Half-Life

In another aspect, the present invention provides an oxidised polysaccharide-protein composition or conjugate as described herein wherein the circulatory half-life ($t_{1/2}$) of a protein that is conjugated is enhanced relative to the circulatory half-life of a non-conjugated protein.

In another aspect, the present invention provides an oxidised polysaccharide-protein composition or conjugate as described herein wherein the circulatory half-life ($t_{1/2}$) or bioactivity of a protein that is conjugated is enhanced relative to the circulatory half-life or activity of a non-conjugated protein by gradually releasing the protein from the conjugate over time.

Suitably the composition allows gradual release of an active protein in circulation. Suitably the composition allows gradual release of an active protein in circulation at physiological pH. Suitably the gradual release occurs by processes such as non-enzymatic hydrolysis or transimination under physiological conditions. Suitably oxidised polysaccharides with varying degrees of oxidation as described herein are conjugated to the protein to allow gradual release of the protein in circulation. Suitably oxidised polysaccharides with varying weight average molecular weights as described herein are conjugated to the protein to allow gradual release of the protein in circulation.

Uses

In a further aspect, there is provided a use of a polysaccharide as described herein in the manufacture of a medicament comprising an oxidised polysaccharide-protein composition, wherein the oxidised polysaccharide is present in the composition in an amount sufficient to prolong the bioavailability and/or bioactivity of the protein in the circulation of a subject.

In a further aspect, there is provided a use of an oxidised polysaccharide-protein composition as described herein in the manufacture of a medicament wherein the circulatory half-life ($t_{1/2}$) or bioactivity of a protein that is conjugated is enhanced relative to the circulatory half-life of a non-conjugated protein.

In a further aspect there is provided a use of an oxidised polysaccharide-protein composition as described herein in the manufacture of a medicament wherein the composition comprises a conjugate such that the circulatory half-life ($t_{1/2}$) or bioactivity of a protein that is conjugated is enhanced relative to the circulatory half-life of a non-conjugated protein.

In a further aspect, there is provided a use of a composition comprising:
  (i) an oxidised polysaccharide-protein conjugate as described herein; and
  (ii) non-conjugated protein;
in the manufacture of a medicament for the treatment of a disease,
wherein following administration of the composition the non-conjugated protein (ii) provides initial activity and the conjugated protein (i) provides sustained activity.

The conjugates, compositions and processes can be used as follows (either independently or in combinations):
  as a therapeutic or diagnostic agent for human use.
  to increase the half-life of the protein.
  to increase the activity of the protein in vitro.
  to preserve the activity of the protein in vitro.
  to increase the activity of the protein in vivo.
  to preserve the activity of the protein in vivo.
  to sustain the activity of the protein.
  to sustain the activity of the protein wherein the sustained activity is a result of the release of protein in plasma.
  to delay the activity of the protein.
  to administer the protein with reduced activity compared to non-conjugated protein, wherein the protein activity is recovered or increased following administration.
  to administer an enzyme with reduced total specific activity compared to non-conjugated enzyme, wherein the total specific activity increases following administration.
  to provide a latent form of an enzyme, which becomes more active during circulation in the body.
  to provide a form of protein that has reduced ability to interact with endogenous activating or inhibiting agents, wherein this ability is recovered following administration.
  to provide a form of protein that has reduced ability to interact with endogenous substrates or receptors or ligands, wherein this ability is recovered following administration.
  to stabilize the protein.
  to temporarily decrease activity of the protein.
  to increase solubility of the protein.

In one aspect, there is provided the use of an oxidised polysaccharide-protein composition described herein to solubilise insulin.

Polysaccharide

Preferably the polysaccharide is a polysaccharide that contains essentially no 1,2,3-triol monomer units (defined as R—CHOH—CHOH—CHOH—R'). 1,2,3-triol monomer units are also known as alpha-beta-gamma-triol monomer units.

The proviso that the polysaccharide contains essentially no 1,2,3-triol monomer units means that preferably less than about 20% of the total polysaccharide monomer units are 1,2,3-triol monomer units. Preferably less than about 15% of the total polysaccharide monomer units are 1,2,3-triol monomer units; preferably less than about 10%; preferably less than about 5%; preferably less than about 3%; preferably less than about 2%; preferably less than about 1% are 1,2,3-triol monomer units.

The amount of 1,2,3-triol monomer units may be calculated from a consideration of the particular polysaccharide being used. For example, hydroxyethyl starch (HES) is made from natural corn starch amylopectin and consists of D-glucose monomers linked via linear α1,4 linkages. Typically in HES, approximately half of the glucose monomers are hydroxyethylated at one or more of their hydroxyl groups through an industrial hydroxyethylation process, to minimize degradation of the HES by amylase in vivo. Higher or lower hydroxyethylation ratios may also be used to prepare HES. The α1,4 linked glucose monomers (linked to neighboring glucose monomers at both the C1 and C4 hydroxyl groups, and also at C6 if at a branch point) contain vicinal diol groups (at C2 and C3), but no 1,2,3-triol groups. The branch end points do contain 1,2,3-triol groups (at C2, C3 and C4) and can form alpha-hydroxy aldehyde groups upon oxidation, which would undergo the Amadori rearrangement if they react with protein. Likewise, the first monomer in the polymer also contains a 1,2,3-triol group (at C1, C2 and C3).

Relevant information for calculating the amount of 1,2,3-triol monomer units such as the branching frequency may be estimated from structural studies using a combination of periodate oxidation and hydrolysis followed by analysis of formic acid, formaldehyde, and other fragments (for example, see "Periodate Oxidation of Diol and Other Functional Groups" by Glenn Dryhurst, Vol. 2 in the series "Monographs in Organic Functional Group Analysis", Pergamon Press, 1970).

The branching frequency in HES is 1 in every 17-20 monomers. Hence, ~5-6% of all glucose monomers in HES would be end points. Not all of these would contain 1,2,3-trial groups, however, because of the hydroxyethylation in HES. Since only ~5-6% of glucose monomers are end groups, and half of these are hydroxyethylated, and because modification of the C2 hydroxyl group accounts for at least two-thirds of hydroxylethylation in HES, then ~3% of HES monomers will contain 1,2,3-triol groups.

Preferably, the polysaccharide is selected from cellulose, pectin, starch and hydroxyhydrocarbyl derivatives thereof.

Preferably the polysaccharide is selected from cellulose, pectin, starch and hydroxyalkyl derivatives thereof. In polysaccharides containing 1,2,3-triol groups, hydroxyalkylation of one or more of the hydroxyl groups in the triol will prevent oxidation of the triol, and prevent the formation of alpha-hydroxy aldehyde groups upon oxidation.

Preferably, the polysaccharide is selected from starch and hydroxyhydrocarbyl derivatives thereof; more preferably the polysaccharide is selected from starch and hydroxyalkyl starch.

Preferably, the polysaccharide is hydroxyethyl starch.

The polysaccharide can be selected from polysaccharides containing vicinal diol groups capable of being oxidized to form dialdehydes, and excluding polysaccharides such as dextran and other similar polysaccharides that, following oxidation, can potentially form irreversible linkages with proteins via the Amadori Rearrangement.

A wide range of natural and modified polysaccharides, varying in size and chemical properties, are available.

The polysaccharide to be used in the present invention may optionally be modified prior to oxidation to alter its stability and biodistribution properties, for example by hydroxyethylation, and by selection of the degree and location of these modifications.

A wide range of proteins may benefit from the various modifications of the polysaccharide, including those requiring release of unmodified protein for optimal activity, proteins benefiting from polymerization to increase activity or for multiple presentations of the protein on the conjugate surface, or to increase half-life and lower clearance. Through appropriate design, the polysaccharide modification may be ideally suited for increasing enzyme half-life while maintaining activity, or masking activity until release.

Preferably the oxidized polysaccharides are polyfunctional, meaning that more than one sugar monomer is oxidized. Where more than one sugar monomer is oxidized, more than two aldehyde groups are formed in the polysaccharide. Polyfunctionality permits polymerization through the polysaccharide, or permits multiple points of attachment between the oxidized polysaccharide and the protein. The degree of polyfunctionality of the oxidized polysaccharide is controlled by the degree of oxidation of the polysaccharide; higher levels of oxidation produce higher levels of polyfunctionality. A higher polyfunctionality can provide for more attachment sites between the oxidized polysaccharide and the protein, and thereby influence the degree of modification and rate of release of the protein from the oxidized polysaccharide, with a greater number of attachment points providing a slower rate of release of the protein.

Preferably, the polysaccharide is a branched polysaccharide. Preferably the degree of branching occurs at less than 1 in 30 monomer units; preferably less than 1 in 25 monomer units; preferably less than 1 in 20 monomer units; preferably less than 1 in 15 monomer units; preferably less than 1 in 10 monomer units; preferably less than 1 in 5 monomer units.

Hydroxyhydrocarbyl Derivatives

Hydroxyhydrocarbyl derivatives of polysaccharides are derivatives where a —OH group of the polysaccharide has been replaced with a —O—$R_1$—OH group, wherein —$R_1$— is a hydrocarbyl group.

The term "hydrocarbyl group" as used herein means a group comprising at least C and H. Also, the hydrocarbyl group may optionally comprise one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred embodiment of the present invention, the hydrocarbyl group is a hydrocarbon group.

Here the term "hydrocarbon" means any one of an alkyl group, an alkenyl group, an alkynyl group, an acyl group. The alkyl group, an alkenyl group, an alkynyl group, an acyl group groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably, the hydroxyhydrocarbyl group is a hydroxyalkyl group.

Preferably, the degree of substitution of the hydroxyhydrocarbyl group in the polysaccharide is from about 0.05 to about 0.9; preferably from about 0.09 to about 0.8; preferably from about 0.1 to about 0.7; preferably from about 0.2 to about 0.6.

Hydroxyalkyl Derivatives

Hydroxyalkyl derivatives of polysaccharides are derivatives where a —OH group of the polysaccharide has been replaced with a —O—$R_2$—OH group, wherein —$R_2$—OH is a hydroxyalkyl group.

Where a hydroxyalkyl group is present, preferably the hydroxyalkyl group has from 1 to 10 carbon atoms. The hydroxyalkyl group may be linear or branched. Preferably the hydroxyalkyl group is selected from hydroxymethyl, hydroxyethyl, hydroxypropyl and hydroxybutyl groups. More preferably the hydroxyalkyl group is a hydroxyethyl group.

Preferably the degree of substitution of the hydroxyalkyl group in the polysaccharide is from about 0.05 to about 0.9; preferably from about 0.09 to about 0.8; preferably from about 0.1 to about 0.7; preferably from about 0.2 to about 0.6.

Degree of Oxidation

Preferably, the degree of oxidation of the oxidised polysaccharide is from 1 to 100%; more preferably from 10 to 100%.

In some aspects, preferably the degree of oxidation of the oxidised polysaccharide is at least about 20%; at least about 25%; at least about 30%; at least about 40%; at least about 50%; at least about 60%; at least about 70%; at least about 75%; at least about 80%; at least about 90%.

In one aspect, preferably the degree of oxidised polysaccharide is 50% or 100%.

Weight Average Molecular Weight of the Polysaccharide

Preferably, the weight average molecular weight of the polysaccharide is from about 1 to about 2000 kDa. Preferably the weight average molecular weight of the polysaccharide is from about 8 to about 2000 kDa; preferably from about 10 to about 1000 kDa; preferably from about 25 to about 750 kDa; preferably from about 50 to about 500 kDa; preferably from about 100 to about 400 kDa; preferably from about 125 to about 250 kDa.

In one aspect the weight average molecular weight of the polysaccharide is about 1, about 10, about 25, about 70, about 125.8, about 130, about 200, about 250 or about 450 kDa, Preferably the weight average molecular weight of the polysaccharide is about 200 kDa.

The weight average molecular weight (WAMW) of the polysaccharide can be selected to control molecular weight of the composition, circulatory half-life and biodistribution, as well as stability and protein load. Polydispersity of the polysaccharide molecular weight can also be selected with similar effect on protein properties.

Oxidised Polysaccharide

Preferably the oxidised polysaccharide contains essentially no alpha-hydroxy aldehyde units.

This proviso that the oxidised polysaccharide contains essentially no alpha-hydroxy aldehyde units means that preferably less than about 20% of the total oxidised polysaccharide monomer units contain alpha-hydroxy aldehyde units. Preferably less than about 15% of the total oxidised polysaccharide monomer units contain alpha-hydroxy aldehyde units; preferably less than about 10%; preferably less than about 5%; preferably less than about 3%; preferably less than about 2%; preferably less than about 1%.

The amount of alpha-hydroxy aldehyde units may be calculated from a consideration of the particular polysaccharide being used. For example, hydroxyethyl starch (HES) is made from natural corn starch amylopectin and consists of D-glucose monomers linked via linear $\alpha 1,4$ linkages. Typically in HES, approximately half of the glucose monomers are hydroxyethylated at one or more of their hydroxyl groups. Higher or lower hydroxyethylation ratios may be used to prepare HES. The $\alpha 1,4$ linked glucose monomers (linked to neighboring glucose monomers at both the C1 and C4 hydroxyl groups, and also at C6 if at a branch point) contain vicinal diol groups (at C2 and C3), but no 1,2,3-triol groups. Oxidation of the vicinal diols does not produce alpha-hydroxy aldehydes, which are required for the Amadori rearrangement to occur upon reaction with protein. The branch end points do contain 1,2,3-triol groups (at C2, C3 and C4) and can form alpha-hydroxy aldehyde groups upon oxidation, which would undergo the Amadori rearrangement if they react with protein. Likewise, the first monomer in the polymer also contains a 1,2,3-triol group (at C1, C2 and C3).

A method of measuring the degree of hydroxyalkylation may be found from Sommermeyer, K., Cech, F., Schmidt, M., Weidler, B.: "Hydroxyethyl starch in clinical use: A physical-chemical characterization" (German Original), Krankenhauspharmazie 8: 271 (1987).

The branching frequency in HES is 1 in every 17-20 monomers. Hence, ~5-6% of all glucose monomers in the starch would be end points. Not all of these would be oxidizable, however, because of the hydroxyethylation in HES. Hydroxyethylation of any of the C2, C3 or C4 hydroxyl groups (members of the 1,2,3 triol) of an end monomer will prevent oxidation to an alpha-hydroxy aldehyde. Since only ~5-6% of glucose monomers are end groups, and half of these are hydroxyethylated, and because modification of the C2 hydroxyl group accounts for at least two-thirds of hydroxylethylation in HES, then ~3% of HES monomers could be oxidized to form alpha-hydroxy aldehydes. In other word, in a typical HES compound only ~3% of HES monomers could form irreversible linkages with proteins.

Alpha-hydroxy aldehyde units may be formed by the partial oxidation of 1,2,3-triols.

Preferably the oxidised polysaccharide has two or more sites for conjugation with the protein. Thus, preferably the oxidised polysaccharide allows multidentate attachment to the protein.

Ratio of Oxidised Polysaccharide to Protein

Preferably the ratio of oxidised polysaccharide to protein is from 0.01:1 to 100:1; preferably the ratio is from 0.1:1 to 20:1; preferably the ratio is from 0.2:1 to 17.5:1; preferably from 0.3:1 to 16:1; preferably from 0.4:1 to 15:1; preferably from 0.5:1 to 12:1; preferably from 0.6:1 to 10:1; preferably from 0.7:1 to 9:1; preferably from 0.8:1 to 8:1.

Depending on the oxidised polysaccharide to protein ratio selected, the protein can be substantially modified with the polysaccharide to limit recognition or activity of the protein, or the protein can be polymerized through conjugation to the polysaccharide, or the protein can be presented on the outside of the oxidised polysaccharide such that recognition required for bioactivity is not impaired.

Protein

The protein component of the composition can be selected from proteins, peptides and derivatives of components thereof containing amino groups capable of reacting with aldehyde groups to form imine bonds, including proteins meeting this criteria that are described in Learner et al., Nature Reviews 2008; 7: 21-39. Proteins suitable for modification include those from various mechanistic classes (e.g., proteins replacing missing or deficient proteins, augmenting or interfering with existing pathways, providing novel function or activity, vaccines or diagnostics), functional classes (e.g., signaling, regulatory, structural, enzymatic, antibodies), structural classes (monomeric, polymeric [covalently vs. non-covalently associated], glycosylated), therapeutic classes (e.g., hormone deficiency, hemostasis and thrombosis, metabolic enzyme deficiency, pulmonary and gastrointestinal disorder, immunodeficiency, hematopoiesis, fertility, immunoregulation, endocrine disorders, growth regulation, cancer, transplantation, infectious disease, detoxification) and those proteins that have been modified using PEG (e.g., interferons, G-CSF, GM-CSF, adenosine deaminase, asparaginase, growth hormones, certolizumab, hematide, uricase), fusion proteins (e.g., interferon, tissue inhibitor metalloproteinase, interleukin, hormones), or in encapsulated forms.

Preferably, the or each protein is selected from an antibody, a cytokine, an enzyme, a peptide, a growth factor and a regulatory protein. Preferably the protein is selected from a cytokine and an enzyme.

Preferably, the or each protein is an antibody or an active fragment or homologue thereof. Preferably the antibody is selected from anti-tumour necrosis factor alpha antibody (Anti-TNFα), CD163 antibody, anti-VEGF, anti-thrombin antibody, anti-CD20 antibody, anti-IgG1 antibody, anti-HER2 antibody, anti-CD33 antibody, anti-IgG2a antibody and anti-EGFR antibody.

Preferably, the or each protein is a cytokine. Preferably the cytokine is selected from interferon (IFN), erythropoietin (EPO) and granulocyte-colony stimulating factor (G-CSF).

Preferably, the or each protein is an enzyme. Preferably the enzyme is selected from uricase, elastase, streptokinase, asparaginase and beta-glucocerebrosidase.

Preferably, the or each protein is a growth factor. Preferably the growth factor is insulin.

Preferably, the or each protein is a regulatory protein. Preferably the regulatory protein is selected from C1 esterase inhibitor and alpha-1 antitrypsin.

For some proteins the activity is dependent on interaction of a protein site with substrates, co-factors, inhibitors, activators, receptors, ligands, allosteric modulators or other interacting molecules. The protein site for such interaction may be obstructed by steric hindrance or direct modification by the polysaccharide in the conjugate, or by other protein molecules in a composition or formulation comprising the conjugate, to result in decreased activity of the protein. Upon release of the protein from the conjugated form, steric hindrance is removed, such that activity increases relative to the conjugated form of the protein. This property of the composition may be especially pronounced in cases where the interacting molecule is not small enough to access, or is blocked from, the protein's reactive site when the site is hindered in such a way to prevent access.

In the case where the protein activity is dependent on intramolecular movement (at the secondary, tertiary or quaternary level), or is dependent on interaction between subunits of the protein, this movement or interaction may be obstructed by steric hindrance or direct modification by the polysaccharide in the conjugate, or by other protein molecules in a composition or formulation comprising the conjugate, to result in decreased activity of the protein. Upon release of the protein from the conjugated form, steric hindrance is removed, such that activity increases relative to the conjugated form of the protein.

Multiple copies of the protein of interest may be incorporated into the conjugate, which may improve recognition events in which multiple local stimuli by the protein are required or are beneficial, such as with certain cell surface receptors.

Proteins and peptides universally contain amino groups that may be used to attach the protein to an oxidised polysaccharide without the need for activating agents or additional chemical linkers.

The protein may comprise more than one amino group and may be conjugated to the oxidised polysaccharide by one or more imine bonds. The protein may be conjugated to the oxidised polysaccharide by two or more imine bonds.

Preferably, the oxidised polysaccharide-protein conjugate comprises a protein whose solubility is increased in the conjugate as compared to the non-conjugated protein.

Preferably, the or each protein is selected from EPO, G-CSF, uricase, beta-glucocerebrosidase, alpha-galactosidase, C-1 inhibitor, streptokinase, DNAseI, alpha-1 antitrypsin, asparaginase, arginine deiminase, Factor IX, Factor VIIa, Factor VIII, Factor IIa (thrombin), anti-TNF-alpha antibody, tissue plasminogen activator, human growth hormone, superoxide dismutase, catalase, CD163 antibody, anti-VEGF, anti-thrombin antibody, anti-CD20 antibody, anti-IgG1 antibody, anti-HER2 antibody, anti-CD33 antibody, anti-IgG2a antibody, anti-EGFR antibody, histone, interferon, insulin, albumin and mixtures thereof.

Preferably, the or each protein has a weight average molecular weight of greater than about 1 kDa; preferably greater than 8 kDa; preferably greater than 10 kDa; preferably greater than 20 kDa; preferably greater than 30 kDa; preferably greater than 40 kDa; preferably greater than 50 kDa.

Preferably, the or each protein has a weight average molecular weight of from 8 kDa to 1000 kDa; preferably from 20 kDa to 900 kDa; preferably from 50 to 800 kDa.

Preferably, the histone is histone H1.

In one aspect, the or each protein is a labeled protein. Suitably, the protein is labeled with a fluorescent label.

Concentration of Protein

Preferably the reaction concentration of protein in step (b) is from about 0.01 to about 10 g/L; preferably from about 0.1 to about 5 g/L; preferably from about 0.2 to about 4 g/L; preferably from about 0.3 to about 2 g/L; preferably from about 0.5 to about 1.5 g/L; preferably from about 0.8 to about 1.2 g/L.

Method

Preferably, the method comprises the step:
(a) selecting a polysaccharide that contains essentially no 1, -2, -3-triol monomer units and oxidising said polysaccharide with an oxidising agent to form an oxidised polysaccharide; and
(b) reacting the oxidised polysaccharide with a protein to form a composition comprising a conjugate wherein the oxidised polysaccharide and the protein are conjugated via one or more imine bonds.

Optionally, the oxidised polysaccharide may be purified to remove the oxidizing agent and its by-products. This purification may comprise the step of diafiltration using a molecular weight cut-off membrane. Suitable membranes include 1 kDa, 5 kDa, 10 kDa, 50 kDa and 100 kDa molecular weight cut-off membrane.

Preferably, the oxidised polysaccharide is reacted with a protein in step (b) in the absence of a molecular crowding agent.

Preferably, the oxidised polysaccharide is reacted with a protein in step (b) in the absence of a reducing agent.

Preferably, the oxidised polysaccharide is reacted with a protein in step (b) in the absence of a molecular crowding agent and in the absence of a reducing agent.

Optionally, the composition formed in step (b) may be purified to remove ions and polysaccharide-based components below a selected molecular weight. This purification may comprise the step of dialyzing a solution containing the conjugate against a solvent using a dialysis membrane or by diafiltration. Suitably the solvent is phosphate-buffered saline or another physiologically acceptable buffer. Suitably the dialysis membrane is selected with a 2, 3.5, 7, 10, 20, 50 or 100 kDa molecular weight cut-off. Suitably the dialysis membrane has a 10 kDa molecular weight cut-off.

In one aspect, the oxidised polysaccharide is reacted with a protein in step (b) in the presence of at least one further protein such that the oxidised polysaccharide-protein composition comprises more than one protein and each protein is conjugated to the oxidised polysaccharide via one or more imine bonds. In this aspect, preferably there is one further protein. Suitably, the protein is streptokinase and the further protein is albumin.

Optionally, the composition may be purified by chromatography.

Optionally, the composition may be a purified molecular weight fraction following the removal of low and/or high molecular weight components.

Optionally, the method may comprise a further step (c) of freeze-drying the composition, or formulating the composition at a concentration, pH and ionic strength that stabilizes the composition.

Oxidising Agent

Preferably the oxidising agent is a periodate compound. Preferably the periodate compound is an alkali metal periodate compound. Suitable oxidizing agents are selected from lithium periodate, sodium periodate and potassium periodate.

Preferably the oxidising agent is sodium periodate.

pH

Preferably step (b) is carried out at a pH of from 6 to 10 at room temperature (26° C.); preferably a pH of from 6.5 to 9; preferably a pH of from 7 to 8.

In some aspects, the pH of the oxidised polysaccharide-protein composition is lowered to a pH of from 5 to 6 (as measured at room temperature 25° C.) for formulations purposes.

Reaction Time

Preferably the oxidised polysaccharide is reacted with a protein in step (b) for from 0.01 to 100 hours; preferably from 0.01 to 80 hours; preferably from 0.01 to 72 hours; preferably from 0.01 to 48 hours; preferably from 0.01 to 36 hours; preferably from 0.02 to 24 hours.

Temperature

Preferably step (a) is carried out at a temperature of less than 20° C.; preferably less than 15° C.; preferably less than 10° C.; preferably less than 5° C.

Preferably step (b) is carried out at temperature of at least 5° C.; preferably at least 10° C.; preferably at least 15° C.; preferably at least 20° C.

In one aspect, preferably step (b) is carried out at temperature of from 5 to 50° C.; preferably from 10 to 48° C.; preferably from 15 to 45° C.; preferably from 20 to 42° C.; preferably from 25 to 40° C.

Treatment or Diagnosis of a Disease or Condition

As discussed herein, the conjugate or compositions containing the conjugate may be used for the treatment or diagnosis of a range of disorders. The disorder may be selected from oncology, infectious disease, metabolic disorders, cardiovascular disorders.

As discussed herein, the conjugate or compositions containing the conjugate may be used for the treatment or diagnosis of a disease or condition. The disease or condition may suitably be selected from hormone deficiency, hemostasis, thrombosis, metabolic enzyme deficiency, pulmonary disorder, gastrointestinal disorder, immunodeficiency, hematopoiesis, fertility disorders, immunoregulation, endocrine disorders, hemophilia, shock, growth regulation, cancer, transplantation, infectious disease, inflammation and detoxification.

Preferably the disorders/diseases or condition may suitably be selected from hepatitis C virus (HCV) infection, acute lymphoblastic leukemia (ALL), chronic obstructive pulmonary disorder (COPD), alpha-1 antitrypsin (AAT) deficiency, anemia, chronic hyperuricemia, hemophilia, hemorrhage, chemotherapy-induced neutropenia, Gaucher's disease, Fabry's disease, hereditary angioedema, malignant melanoma, hepatocellular carcinoma (HCC), reperfusion injury, myocardial infarction, pulmonary embolism, psoriasis, Crohn's disease, rheumatoid arthritis, ulcerative colitis, cystic fibrosis, hemophilia A, hemophilia B, von Willebrand disease, diabetes, sepsis, hypovolemic shock and growth hormone deficiency.

Preferably the composition is administered to a subject and the protein is released from the conjugate over time such that the circulatory half-life of the protein that is conjugated is enhanced relative to the circulatory half-life of non-conjugated protein Other Features Preferably, the oxidised polysaccharide is reacted with a protein in step (b) in the absence of a molecular crowding agent. Preferably, the oxidised polysaccharide is reacted with a protein in step (b) in the absence of a macromolecular crowding agent. For the purposes of this specification a macromolecular crowding agent is defined herein as a compound that attracts water and allows molecules to aggregate.

Examples of macromolecular crowding agents are soluble, linear polymers such as polyvinylpyrrolidone, polyehthylene glycol, dextran, nonylphenol-thoxylates, polyvinyl alcohol and mixtures thereof.

Optionally, the composition or conjugate may be freeze-dried, or formulated at a concentration, pH and ionic strength that stabilizes the composition or conjugate.

Size and in vivo stability of a protein-polysaccharide composition can be controlled through proper selection of degree of hydroxyethylation or other modification of the polysaccharide (e.g., oxidation), which will control the rate of dissociation or degradation of the polysaccharide and release of the protein. Additionally, size and in vivo stability of a protein-polysaccharide composition can be controlled through proper selection of pH of conjugation, protein concentration during conjugation, temperature during conjugation, duration of conjugation, excipients added after conjugation and formulation of the conjugate.

In a further aspect, there is provided an oxidised polysaccharide-protein composition or conjugate as described herein wherein the degree of oxidation of the oxidised polysaccharide, and/or the weight average molecular weight of the polysaccharide, and/or ratio of oxidised polysaccharide to protein, and/or degree of substitution of the hydroxyhydrocarbyl group in the polysaccharide, and/or the polydispersity of the polysaccharide is used to control:

activity of the protein in the composition;
activity of the conjugated protein;
activity of the released protein;
circulatory half-life of the protein;
rate of release of active protein from the conjugate;
stability of the conjugate vs degradation;
solubility of the conjugated protein In a further aspect, there is provided an oxidised polysaccharide-protein conjugate or a composition as described herein wherein the conjugate is capable of releasing protein in presence of plasma components.

In a further aspect, there is provided an oxidised polysaccharide-protein conjugate or a composition as described herein wherein the linkage between the protein and the oxidized polysaccharide is dissociated by processes such as non-enzymatic hydrolysis and transimination under physiological conditions.

In a further aspect, there is provided an oxidised polysaccharide-protein conjugate, a composition or processes as described herein for selected conjugate stability in plasma.

In a further aspect, there is provided an oxidised polysaccharide-protein conjugate, a composition or processes as described herein for selected conjugate stability in solution, with majority of protein maintained in the conjugated form or maintenance of a selected non-conjugated:conjugated protein ratio, optionally controlled by selection of pH, ionic strength or concentration of the composition.

In a further aspect, there is provided an oxidised polysaccharide-protein conjugate or a composition as described herein wherein the protein is an enzyme and the conjugate or composition has a masked, latent, dormant or preserved enzyme activity.

In a further aspect, there is provided an oxidised polysaccharide-protein conjugate, a composition or processes as described herein for increasing in vivo half-life or bioactivity of the protein.

In a further aspect, there is provided a method of reversibly conjugating a protein to an oxidised polysaccharide comprising the steps of preparing an oxidised polysaccharide-protein composition as described herein, and dissolving the oxidised polysaccharide-protein composition in a solvent.

Specific Combinations

Suitably the conjugates, compositions, methods and uses as described herein may comprise a polysaccharide selected from starch and hydroxyethyl starch, and a protein that is interferon. Suitably the degree of oxidation of the oxidised polysaccharide is selected from 1, 10, 25, 50, 75 and 100% to increase the half-life of interferon. Suitably hydroxyethyl starch with a weight average molecular weight from about 1, 10, 25, 70, 200, or 450 kDa is used to increase the half-life of interferon and/or allow gradual release of the active interferon in circulation. Suitably starch with a weight average molecular weight of about 125.8 kDa is used to increase the half-life of interferon and/or allow gradual release of the active interferon in circulation. Suitably the composition has increased activity half-life/duration of activity compared to interferon.

The amino groups of interferon may be conjugated to the oxidised starch or hydroxyethyl starch by more than one imine bond.

Suitably the conjugates, compositions, methods and uses as described herein may comprise a 200 kDa hydroxyethyl starch-protein formulation wherein the protein is an enzyme which has reduced activity in the conjugated form, compared to the enzyme released from the conjugate. Suitably the enzyme is selected from uricase, elastase, asparaginase, streptokinase and beta-glucocerebrosidase.

Suitably the conjugates, compositions, methods and uses as described herein may comprise a 200 kDa hydroxyethyl starch-protein formulation wherein the protein is a regulatory protein. Suitably the regulatory protein is selected from C1 esterase inhibitor and alpha-1 antitrypsin.

Suitably the conjugates, compositions, methods and uses as described herein may comprise a 200 kDa hydroxyethyl starch-protein formulation wherein the protein is a cytokine. Suitably the cytokine is selected from interferon (IFN), erythropoietin (EPO) and granulocyte-colony stimulating factor (G-CSF).

Suitably the conjugates, compositions, methods and uses as described herein may comprise a 200 kDa hydroxyethyl starch-protein formulation wherein the protein is an antibody. Suitably the antibody is selected from anti-tumour necrosis factor alpha antibody (Anti-TNFα), anti-thrombin and anti-CD163. Other examples include Rituxan® (anti-CD20) Idec-Genentech, Mylotarg® (anti-CD33) Wyeth, Avastin® (anti-VEGF), anti-IgG1 (Herceptin®) Genentech, anti-HER2 (Herceptin®) Genentech, anti-IgG2a (Bexxar®) Corixam-GSK and anti-EGFR (Erbitux®) Imclone.

Hydroxyethyl Starch

A preferred polysaccharide is hydroxyethyl starch. Hydroxyethyl starch has been widely used as an approved blood volume expander for decades and has been infused in large volumes (~3 g hydroxyethyl starch/kg body weight) into a large number of and wide range of patients.

Hydroxyethyl starch is an approved modified form of naturally occurring starch and may therefore be more biologically compatible (e.g., readily metabolized) than other macromolecules, especially those that are synthetic.

The hydroxyethyl starch-protein link involves the direct interaction of aldehydes on the oxidised hydroxyethyl starch with amino groups on the protein to form an imine bond, with no intervening chemical linker.

Large conjugates with correspondingly increased half-life and protein load are possible for hydroxyethyl starch modification, owing to the high molecular weights of hydroxyethyl starch available, and because of the possibility of oligomerization. The hydroxyethylation of starch increases the stability of the starch by impairing amylase degradation in vivo.

Suitably conjugates of oxidized hydroxyethyl starch and protein may have
- up to 100% of vicinal dials in the hydroxyethyl starch have been oxidized to aldehydes, or
- the protein contains amino groups capable of forming imine linkages with the aldehydes of the oxidized hydroxyethyl starch, or
- the majority of protein is conjugated to the oxidized hydroxyethyl starch through imine linkages, or
- activity of the conjugated protein may be decreased relative to non-conjugated protein, or
- the majority of the conjugated protein is capable of being released from the conjugate, or
- activity of the released protein is greater than or equal to the conjugated protein, or
- activity of the released protein is less than the conjugated protein (in the possible case where HES bulk aids in receptor recognition or binding of substrates, etc.).

Further aspects of the invention are provided in the following numbered paragraphs.

(1) A method of preparing an oxidised polysaccharide-protein composition comprising the steps of:
 (a) oxidising a polysaccharide with an oxidising agent to form an oxidised polysaccharide; and
 (b) reacting the oxidised polysaccharide with a protein to form a composition comprising a conjugate wherein the oxidised polysaccharide and the protein are conjugated via one or more imine bonds; and
 (c) optionally lowering the pH of the oxidised polysaccharide-protein conjugate to a pH of from 5 to 6 for formulation purposes.

(2) A method according to paragraph (1), wherein with the polysaccharide is a polysaccharide that contains essentially no 1,2,3-trial monomer units.

(3) A method according to paragraph (2) wherein the 1,2,3-triol monomer units are partially or completely alkylated to prevent formation of alpha-hydroxy aldehyde groups upon oxidation of the triol.

(4) A method according to any one of the preceding numbered paragraphs, wherein the oxidised polysaccharide is reacted with a protein in step (b) in the absence of a molecular crowding agent.

(5) A method according to any one of the preceding numbered paragraphs, wherein the oxidised polysaccharide is reacted with a protein in step (b) in the absence of a reducing agent.

(6) A method according to any one of the preceding numbered paragraphs, wherein the polysaccharide is selected from cellulose, pectin, starch and hydroxyhydrocarbyl derivatives thereof.

(7) A method according to any one of the preceding numbered paragraphs, wherein the polysaccharide is selected from cellulose, pectin, starch, hydroxalkyl cellulose and hydroxalkyl starch.

(8) A method according to any one of the preceding numbered paragraphs, wherein the polysaccharide is hydroxyethyl starch.

(9) A method according to any one of the preceding numbered paragraphs, wherein the degree of oxidation of the oxidised polysaccharide is from 1 to 100%.

(10) A method according to any one of the preceding numbered paragraphs, wherein the weight average molecular weight of the polysaccharide is from 1 to 2000 kDa.

(11) A method according to any one of the preceding numbered paragraphs, wherein the ratio of oxidised polysaccharide to protein is from 0.1:1 to 20:1.

(12) A method according to any one of the preceding numbered paragraphs, wherein step (a) is carried out at temperature of less than 10° C.

(13) A method according to any one of the preceding numbered paragraphs, wherein step (b) is carried out at temperature of at least 10° C.

(14) A method according to any one of the preceding numbered paragraphs, wherein the oxidising agent is a periodate compound.

(15) A method according to any one of the preceding numbered paragraphs, wherein the oxidised polysaccharide is reacted with a protein in step (b) in the presence of at least one further protein such that the oxidised polysaccharide-protein composition comprises more that one protein and each protein is conjugated to the oxidised polysaccharide via one or more imine bonds.

(16) A method according to any one of the preceding numbered paragraphs, wherein the or each protein is selected from antibodies, cytokines, enzymes, growth factors and regulatory proteins.

(17) A method according to any one of the preceding numbered paragraphs, wherein the or each protein is selected from erythropoietin (EPO), granulocyte-colony stimulating factor (G-CSF), uricase, beta-glucocerebrosidase, alpha-galactosidase, C-1 inhibitor, streptokinase, DNAseI, alpha-1 antitrypsin, asparaginase, arginine deiminase, Factor IX, Factor VIIa, Factor VIII, Factor IIa (thrombin), anti-TNF-alpha antibody, tissue plasminogen activator, human growth hormone, superoxide dismutase, catalase, CD163 antibody, anti-VEGF, anti-thrombin antibody, anti-CD20 antibody, anti-IgG1 antibody, anti-HER2 antibody, anti-CD33 antibody, anti-IgG2a antibody, anti-EGFR antibody, histone, interferon, insulin, albumin and mixtures thereof.

(18) A method according to any one of the preceding numbered paragraphs wherein the oxidized polysaccharide contains essentially no alpha hydroxyl aldehyde units.

(19) A method according to any one of the preceding numbered paragraphs wherein the oxidised polysaccharide-protein conjugate is less than 0.1 µm in size.

(20) A method according to any one of the preceding numbered paragraphs wherein the oxidised polysaccharide has two or more sites for conjugation with the protein.

(21) A method according to any one of the preceding numbered paragraphs wherein the protein has a weight average molecular weight of greater than about 1 kDa.

(22) A method according to any one of the preceding numbered paragraphs, wherein the oxidised polysaccharide-protein composition further comprises non-conjugated protein.

(23) An oxidised polysaccharide-protein composition obtained by the method of any one of the preceding numbered paragraphs.

(24) An oxidised polysaccharide-protein composition comprising an oxidised polysaccharide and a protein; wherein the oxidised polysaccharide comprises essentially no alpha-hydroxy aldehyde units and wherein the protein is conjugated to the oxidised polysaccharide via one or more imine bonds.

(25) An oxidised polysaccharide-protein composition according to paragraph (22) comprising the features as described in any one of paragraphs (1) to (22).

(26) An oxidised polysaccharide-protein composition for use in the treatment or diagnosis of a disease or condition wherein the protein is conjugated to the oxidised polysaccharide via one or more imine bonds.

(27) An oxidised polysaccharide-protein composition according to paragraph (26) wherein the oxidised polysaccharide contains essentially no alpha-hydroxy aldehyde units.

(28) An oxidised polysaccharide-protein composition according to paragraph (26) or (27), wherein the composition was obtained or obtainable by the method of any one of paragraphs (1) to (22).

(29) An oxidised polysaccharide-protein composition according to any one of paragraphs (26) to (28), wherein the disease or condition is selected from hormone deficiency, hemostasis, thrombosis, metabolic enzyme deficiency, pulmonary disorder, gastrointestinal disorder, immunodeficiency, hematopoiesis, fertility disorders, immunoregulation, endocrine disorders, hemophilia, shock, growth regulation, cancer, transplantation, infectious disease, inflammation and detoxification.

(30) An oxidised polysaccharide-protein composition according to any one of paragraphs (26) to (29), wherein the disease or condition is selected from hepatitis C virus (HCV) infection, acute lymphoblastic leukemia (ALL), chronic obstructive pulmonary disorder (COPD), alpha-1 antitrypsin (AAT) deficiency, anemia, chronic hyperuricemia, hemophilia, hemorrhage, chemotherapy-induced neutropenia, Gaucher's disease, Fabry's disease, hereditary angioedema, malignant melanoma, hepatocellular carcinoma (HCC), reperfusion injury, myocardial infarction, pulmonary embolism, psoriasis, Crohn's disease, rheumatoid arthritis, ulcerative colitis, cystic fibrosis, hemophilia A, hemophilia B, von Willebrand disease, diabetes, sepsis, hypovolemic shock and growth hormone deficiency.

(31) An oxidised polysaccharide-protein composition any one of paragraphs (26) to (30), wherein the composition is administered to a subject and the protein is released from the conjugate over time such that the circulatory half-life of the protein that is conjugated is enhanced relative to the circulatory half-life of non-conjugated protein.

(32) A method of reversibly conjugating a protein to an oxidised polysaccharide comprising the steps of preparing an oxidised polysaccharide-protein composition according to any one of paragraphs (1) to (22), and dissolving the oxidised polysaccharide-protein composition in a solvent.

(33) Use of an oxidised polysaccharide-protein composition according to any one of paragraphs (23) to (25), to solubilise the protein.

(36) Use according to paragraph (33), wherein the protein is insulin,

BRIEF DESCRIPTION OF THE DRAWINGS

The present invention will now be described in further detail by way of example only with reference to the accompanying figures in which.

EXAMPLES

Figure 1:
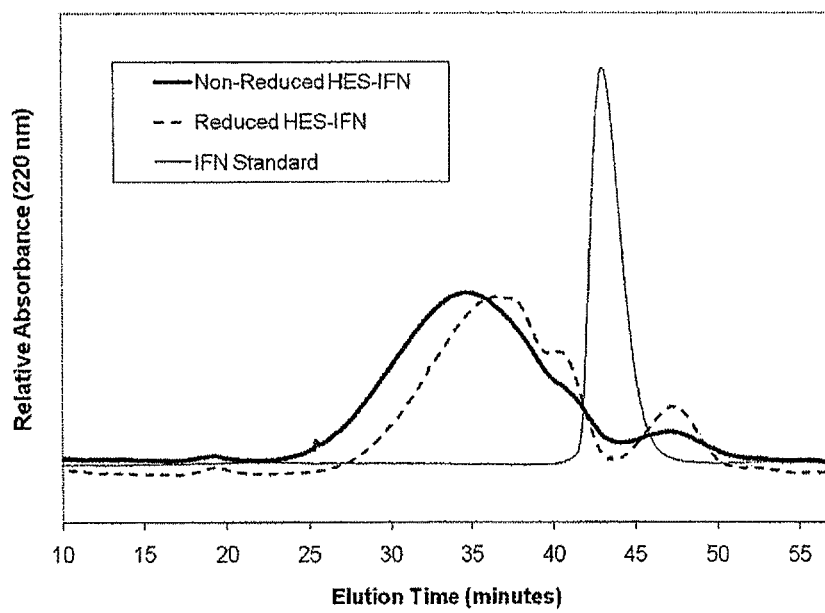
FIG. 1 is a representative chromatogram (HPLC traces of modified IFN).

The present invention will now be described in further detail by way of examples. Although a variety of conditions such as MW of the polysaccharide, degree of oxidation of the polysaccharide, temperature of reaction, pH of reaction, protein concentration, ratio of polysaccharide to protein, and duration of reaction were employed with all proteins, only specific examples are shown.

Preparation of Oxidized Polysaccharides

Example 1

General Procedure to Prepare Oxidised Polysaccharides

The polysaccharide was dissolved by stirring in water. Sufficient sodium periodate ($NaIO_4$) was added to achieve the desired oxidation level and stirred. After a suitable time the reaction mixture was then concentrated and diafiltered against pure water using a low molecular weight cut-off membrane. Alternatively, low molecular weight salts were removed by dialysis, chromatography or other methods. Oxidised polysaccharide concentration of the recovered retentate was determined by lyophilizing aliquots of the retentate and weighing the dried residue.

Example 2

Preparation of Oxidised Hydroxyethyl Starch (oxiHES)

Under aseptic conditions, 10.6 g hydroxyethyl starch (HES, 200 kDa weight-average molecular weight (WAMW), degree of hydroxyethyl substitution 0.5) was dissolved by stirring in 225 mL water overnight while cooling to 4° C. 8.8 g sodium periodate ($NaIO_4$) (1.1 eq. per vicinal diol) was added and stirring continued in the dark at 4° C. The reaction mixture was then concentrated to 100 mL and diafiltered against 10 volumes of water using a 5 kDa molecular weight cut-off (MWCO) polyethersulfone membrane.

The 50% oxidized HES was prepared by the same process, using 10.9 g of HES and 4.1 g $NaIO_4$ (0.5 eq. per vicinal diol). 10 and 25% oxidized HES were similarly prepared, as were oxidized versions of starch (without hydroxyethylation), by using the appropriate amounts of sodium periodate to produce the desired degree of oxidation.

HES and starch samples with weight-average molecular weight (WAMW) values between 1 and 2000 kDa, specifically those with WAMW of 25, 70, 130, 200, 250 and 450 kDa were similarly treated to achieve oxidized polysaccharide materials with oxidation levels of 1, 10, 25, 50, 75 and 100%, by using the appropriate amounts of sodium periodate to produce the desired degree of oxidation.

Example 3

Preparation of 50% Oxidized Starch 10.01 g of starch (degraded waxy maize, 125.8 kDa) was dissolved in 200 mL of water at 4° C. To this was added 5.69 g of sodium periodate ($NaIO_4$:aldyhyde-producing monomer=0.5:1). The mixture was allowed to react for 4 hours at 4° C. The resulting reaction mixture was concentrated and diafiltered against 10 volumes of water using a 5 kDa MWCO membrane. The final oxi-starch solution was concentrated and filtered prior to use. The overall yield was 87%.

Preparation of Oxidized Polysaccharides-Protein Compositions

Example 4

General Procedure to Prepare Oxidised Polysaccharide-Protein Compositions

Aqueous protein solution was combined with oxidized polysaccharide solution and buffer such that the final oxidised polysaccharide:protein molar ratio was between 0.1:1 and 50:1. The protein concentration was between 0.1 and 10 mg/mL. The pH of the reaction was between 6 and 8. The temperature of reaction was between 4° C. and 37° C. The duration of the reaction varied between 5 minutes to 72 h. The molecular weight of the polysaccharide was between 8 and 450 kDa. The degree of oxidation of the polysaccharide was between 10 and 100%. After suitable reaction time to achieve substantial modification of the protein by the oxidized polysaccharide, the reaction mixture was divided for the preparation of the non-reduced and reduced conjugates. Compositions of non-reduced conjugate suitable for in vitro or in vivo use were prepared by dialysis, diafiltration or chromatography to remove low MW salts and to formulate the composition in the required buffer. In some cases the pH was lowered to maintain the desired molecular weight profile by dilution with pH 5 or 5.5 buffer prior to dialysis.

Example 5

Preparation of Reduced Oxidised Polysaccharide-Protein Composition

The reduced conjugate was prepared by combining an aliquot of the oxidized polysaccharide-protein reaction mixture with a suitable reducing agent, such as a combination of sodium acetate solution and sodium cyanoborohydride ($NaBH_3CN$). The reduction reaction mixture was sealed and mixed. Compositions of reduced conjugate suitable for in vitro or in vivo use were prepared by dialysis, diafiltration or chromatography to remove low MW salts and to formulate the composition in the required buffer.

Preparation of Polysaccharide-Protein Compositions: Non-Reduced and Reduced

Polysaccharides with WAMW from 8 to 450 kDa were selected for oxidation as described above. For polysaccharides containing a hydroxethyl group, the degree of hydroxyethylation was selected from 0 to 0.7. The degree of polysaccharide oxidation was selected from 1 to 100%. Oxidized polysaccharide: protein reaction ratio was selected from 0.2:1 to 17.5:1. Reaction times were selected from 0.5 to 72 hours. Reaction pH was selected from a range between 6 and 8. Reaction protein concentration was selected from 0.5 to 10.0 g/L.

Example 6

Preparation of 100% Oxidized HES-Interferon Compositions: Non-Reduced and Reduced 100 μL of a 10 microgram/microliter solution of interferon alpha-2b (IFN) in water was combined with 689 microliter water, 50 microliter 0.9% phosphate-buffered saline (PBS, pH 7.4) and 161 microliter of 100% oxidized HES (64.3 mg/mL, 200 kDa WAMW). The final oxiHES:IFN molar ratio was 1:1. After 24 hr mixing at 25° C., the reaction mixture was divided for the preparation of the non-reduced and reduced compositions. To prepare the non-reduced composition, 440 microliter was diluted with 2.4 mL PBS and dialyzed at 4° C. against PBS using a 10 kDa membrane. The retentate was then filtered (0.22 micrometer) and diluted to 4.4 mL with PBS.

The reduced composition was prepared by combining 500 microliter of the divided reaction mixture with 89 microliter 0.3 M sodium acetate (NaOAc) and 391 microliter freshly prepared 10% sodium cyanoborohydride ($NaBH_3CN$) in water. The reduction reaction mixture was sealed and mixed at 25° C. for 16-24 hr, then combined with 2 mL PBS and dialyzed at 4° C. against PBS using a 10 kDa membrane. The retentate was then filtered (0.22 micrometer) and diluted to 3.9 mL with PBS. The high molecular weight of the IFN-containing reduced and non-reduced conjugates, compared to unmodified IFN, was shown by size exclusion chromatography.

Example 7

Preparation of 50% Oxidized HES-Interferon Compositions: Non-Reduced and Reduced The non-reduced and reduced 50% oxidized HES-IFN compositions were prepared using the 50% oxiHES by a similar process as used for the 100% oxidized HES compositions described above. 100 microliter of a 10 microgram/microliter solution of IFN in water was combined with 215 microliter water, 50 microliter PBS (pH 7.4) and 635 microliter of 50% oxidized HES (116 mg/mL). The final oxiHES: IFN molar ratio was 7.1:1. After 24 h of mixing at 25° C., the reaction mixture was divided and the non-reduced and reduced compositions were prepared as described for the 100% oxidized HES compositions above. The reduced composition was prepared using 250 microliter conjugate, 94 microliter 0.3 M sodium acetate (NaOAc) and 694 microliter $NaBH_3CN$ solution.

Example 8

Preparation of 50% Oxidized Starch-Interferon Conjugate 8 microliter of interferon (IFN) solution (10 microgram/microliter) was conjugated at 1.0 microgram/microliter, with an oxi-HES to IFN ratio of 1.0:1. To this solution was added 56.2 microliter of water, 8 microliters of 1.0 M Bis-Tris buffer, pH 7.0 and 7.8 microliter of oxi-Starch solution prepared as described above (125.8 kDa). Reactions were carried out at 23° C. At 0.5, 1, 2, 6 and 24 hours into conjugation, aliquots of each conjugation mixture were removed and reduced with a 10% solution of $NaBH_3CN$ in water in the presence of NaOAc (30 mM) for 20 hours SDS-PAGE analyses indicated that all IFN was converted to HES-IFN conjugates, with no visible free IFN.

Example 9

Preparation of Polysaccharide-Interferon Compositions: Non-Reduced and Reduced

Non-reduced and reduced compositions of interferon and polysaccharides were prepared as described in the previous examples. Selected examples of conditions used to prepared polysaccharide-IFN compositions are listed in Table 1.

TABLE 1

Selected examples of reaction conditions used to prepare polysaccharide-IFN compositions.

| Table Entry | PS WAMW (kDa) | Hydroxyethyl Substitution (fraction) | PS Oxidation (%) | Rxn PS:IFN Ratio | Rxn Time (h) |
|---|---|---|---|---|---|
| 1 | 450 | 0.7 | 100 | 0.5:1 | 0.5, 2, 6 |
| 2 | 450 | 0.7 | 100 | 1:1 | 0.5, 2, 6 |
| 3 | 200 | 0.5 | 100 | 0.5:1 | 0.5, 2, 6 |
| 4 | 200 | 0.5 | 100 | 1:1 | 0.5, 2, 6, 24 |
| 5 | 200 | 0.5 | 100 | 2:1 | 24 |
| 6 | 200 | 0.5 | 50 | 2:1 | 24 |
| 7 | 200 | 0.5 | 50 | 5:1 | 24 |
| 8 | 200 | 0.5 | 50 | 7.1:1 | 24 |
| 9 | 125.8 | 0 | 10 | 0.2:1 | 0.5, 1, 2, 6, 24 |
| 10 | 125.8 | 0 | 25 | 0.2:1 | 0.5, 1, 2, 6, 24 |
| 11 | 125.8 | 0 | 75 | 0.2:1 | 0.5, 1, 2, 6, 24 |
| 12 | 125.8 | 0 | 10 | 0.5:1 | 0.5, 1, 2, 6, 24 |
| 13 | 125.8 | 0 | 25 | 0.5:1 | 0.5, 1, 2, 6, 24 |
| 14 | 125.8 | 0 | 50 | 0.5:1 | 0.5, 1, 2, 6, 24 |
| 15 | 125.8 | 0 | 75 | 0.5:1 | 0.5, 1, 2, 6, 24 |
| 16 | 125.8 | 0 | 25 | 1:1 | 0.5, 1, 2, 6, 24 |
| 17 | 125.8 | 0 | 50 | 1:1 | 0.5, 1, 2, 6, 24 |

TABLE 1-continued

Selected examples of reaction conditions used to prepare polysaccharide-IFN compositions.

| Table Entry | PS WAMW (kDa) | Hydroxyethyl Substitution (fraction) | PS Oxidation (%) | Rxn PS:IFN Ratio | Rxn Time (h) |
|---|---|---|---|---|---|
| 18 | 70 | 0.5 | 100 | 0.5:1 | 0.5, 2, 6 |
| 19 | 70 | 0.5 | 100 | 1:1 | 0.5, 2, 6 |
| 20 | 70 | 0.57 | 100 | 1:1 | 24 |
| 21[A] | 70 | 0.57 | 100 | 2:1 | 0.5, 1, 2, 6 |
| 22 | 70 | 0.57 | 100 | 17.5:1 | 7, 24, 48, 72 |
| 23 | 70 | 0.57 | 50 | 2:1 | 24 |
| 24 | 70 | 0.57 | 100 | 5:1 | 0.5, 2, 7, 24, 48, 72 |
| 25[A] | 70 | 0.57 | 100 | 5:1 | 0.5, 1, 2, 6 |
| 26[A] | 8 | 0.45 | 100 | 5:1 | 7, 24, 48 |
| 27[A] | 8 | 0.45 | 100 | 17.5:1 | 7, 24, 48 |
| 28 | 8 | 0.5 | 100 | 0.5:1 | 24 |
| 29 | 8 | 0.5 | 100 | 1:1 | 24 |
| 30 | 8 | 0.5 | 100 | 10:1 | 0.5, 2, 6 |
| 31[B] | 8 | 0.5 | 100 | 10:1 | 0.5, 2, 6 |

Reaction temperatures were 23-25° C. unless otherwise specified. Reaction IFN concentration was 1.0 g/L unless otherwise specified. Reaction pH was 7 unless otherwise specified.
[A]Reaction pH was 8
[B]Reaction IFN concentration was 0.5 g/L The reaction conditions in entries 4 (24 hours) and 8 of Table 1 were preferred for the preparation of HES-IFN for in vivo evaluation.

Example 10

General Procedure for Characterization of Oxidised Polysaccharide-Protein Molecular Weight and Total Protein Concentration Oxidised polysaccharide-protein compositions were analysed by size exclusion chromatography (SEC) to determine molecular weight (MW) distribution and to determine free protein content. Samples were eluted on an appropriate SEC column, pre-equilibrated with appropriate elution mobile phase. Elution was carried out at an appropriate flow rate with appropriate mobile phase and detection was at a suitable wavelength. Modification of the protein in the oxidised polysaccharide-protein compositions was evident from the presence of high MW (early retention time) components, and the lower level of unmodified protein (low levels of components with elution time the same as the unmodified protein standard). Unmodified protein content was estimated from the peak area corresponding to the unmodified protein standard. Total protein concentration was determined by comparison of protein amino acid concentrations to an internal standard (amino acid analysis). Non-reduced compositions were shown to contain varying levels of unmodified protein and differing MW distributions, including non-reduced high molecular weight conjugates suitable for increasing the half-life of the protein and permitting release of the protein in active form. Also, compositions containing ratios of unmodified and modified protein suitable for providing immediate and sustained protein activity were identified. These composition parameters were dependent on process variables including polysaccharide WAMW, the degree of oxidation of the polysaccharide, the degree of hydroxyethylation of the polysaccharide, as well as the oxidised polysaccharide:protein ratio and the protein concentration in the reaction.

Example 11

Characterization of HES-IFN Molecular Weight and Total Interferon Concentration

Polysaccharide-IFN compositions were analysed by size exclusion chromatography using an HPLC system to determine molecular weight (MW) distribution and to determine free IFN content. Samples were eluted on a Superdex 200 10×30 mm column, pre-equilibrated with PBS pH 7.4. Elution was carried out at 0.4 mL/min of PBS pH 7.4 and detection was at 220 nm. A representative chromatogram comparing the MW distributions of non-reduced and reduced HES-IFN prepared from 100% oxidized HES, compared to unmodified IFN standard, is shown in FIG. 1.

Modification of the IFN in the HES-IFN compositions is evident from the presence of high MW (early retention time) components with absorption at 220 nm, and the low level of unmodified IFN (low levels of components with absorption at 220 nm with elution time the same as the unmodified IFN standard). In the non-reduced and reduced HES-IFN samples, peaks appearing at ~47 minute elution time were found to be low MW oxiHES components. Unmodified IFN content was estimated from the peak area corresponding to the unmodified IFN standard. Total IFN concentration was determined by comparison of IFN amino acid concentrations to an internal standard (norleucine) concentration following hydrolysis, phenylisothiocyanate (PITC) labelling and chromatographic analysis. Representative IFN concentration data for HES-IFN conjugates prepared using 50% and 100% oxidized HES are listed in Table 2.

TABLE 2

HES-IFN Conjugate Properties.

| Test Article | HES MW (kDa) | HES Oxidation (%) | HES Linkage Type | [IFN] microgram/ millilitre (QAAA)[1] | Free IFN (%) (est.)[2] |
|---|---|---|---|---|---|
| Hb-HES Conjugate (in PBS) | 200 | 100 | Non-reduced | 31.7 | <1 |
| | 200 | 100 | Reduced | 58.7 | <1 |

TABLE 2-continued

HES-IFN Conjugate Properties.

| Test Article | HES MW (kDa) | HES Oxidation (%) | HES Linkage Type | [IFN] microgram/ millilitre (QAAA)[1] | Free IFN (%) (est.)[2] |
|---|---|---|---|---|---|
| | 200 | 50 | Non-reduced | 58.1 | <1 |
| | 200 | 50 | Reduced | 44.8 | <1 |
| Positive Control | IFNα2b in PBS | | | 66.5 | 100 |
| Negative Control | PBS | | | — | — |

[1]QAAA: Quantitative amino acid analysis. IFN concentration was determined by comparison of IFN amino acid concentrations to an internal standard (norleucine) concentration following hydrolysis, phenylisothiocyanate (PITC) labeling and chromatographic analysis.
[2]Unmodified IFN content was estimated by peak area using size exclusion chromatography. Free IFN was identified by comparison of elution time with IFN standard, and estimated percent of free IFN was equal to the free IFN peak area divided by total peak area (220 nm).

Example 12

Determination of Duration of IFN Activity In Vivo for HES-IFN Compositions

To compare the duration of IFN activity of HES-IFN conjugates vs. unmodified IFN, compositions were administered to mice and plasma samples obtained at various time points and assayed for IFN activity. This example uses non-reduced and reduced HES-IFN compositions prepared from 50% and 100% oxidized HES. Male CD1 mice were assigned to one of seven groups (12 mice per group, Table 3). Animals in groups 1 to 6 were injected via the tail vein with HES-IFN compositions or control solutions (0.0035 mL/g). Unmodified IFNα2b was used as a positive control. PBS was used as a negative control, since all test articles and the IFN control were formulated in PBS. Blood was collected via cardiac puncture (terminal) from three mice per group at 15 minutes, 4 hours, 24 hours and 48 hours after the start of test article injection. Blood was also collected from 3 untreated mice as baseline controls. Plasma was prepared from each blood sample and divided into sterile tubes and frozen at −80° C. Aliquots from all 3 animals at each time point were thawed and combined for IFN activity analysis. All aliquots and samples were kept on ice during manipulation. IFN activities were assayed using a standardized viral inhibition assay. Interferon was titrated with the use of the cytopathic effect inhibition assay as described by Rubenstein et al (Rubinstein, S., Familletti, P. C., and Pestka, S. (1981) "Convenient Assay for Interferons," J. Virol. 37, 755-758; Familletti, P. C., Rubinstein, S., and Pestka, S. (1981)" A Convenient and Rapid Cytopathic Effect Inhibition Assay for Interferon," in Methods in Enzymology, Vol. 78 (S. Pestka, ed.), Academic Press, New York, 387-394). In this antiviral assay for interferon about 1 unit/ml of interferon is the quantity necessary to produce a cytopathic effect of 50%. The units are determined with respect to the international reference standard for human interferon alpha A (Hu-IFN-αA) provided by the National Institutes of Health (Pestka, S. (1986) "Interferon Standards and General Abbreviations, in Methods in Enzymology (S. Pestka, ed.), Academic Press, New York 119, 14-23). Activity is measured on Madin-Darby bovine kidney (MDBK) cells with vesicular stomatitis virus (VSV). Plasma and serum IFN activity reported here are for samples thawed and held at 4° C. for 16 hr prior to assay. Since all animals received equal volume doses of each product, and the concentrations of IFN in products were different, IFN activity was corrected for total IFN concentration by dividing the MDBK assay data (U/mL) by the IFN concentrations of the dosed products (microgram/ milliliter).

Figure 2:
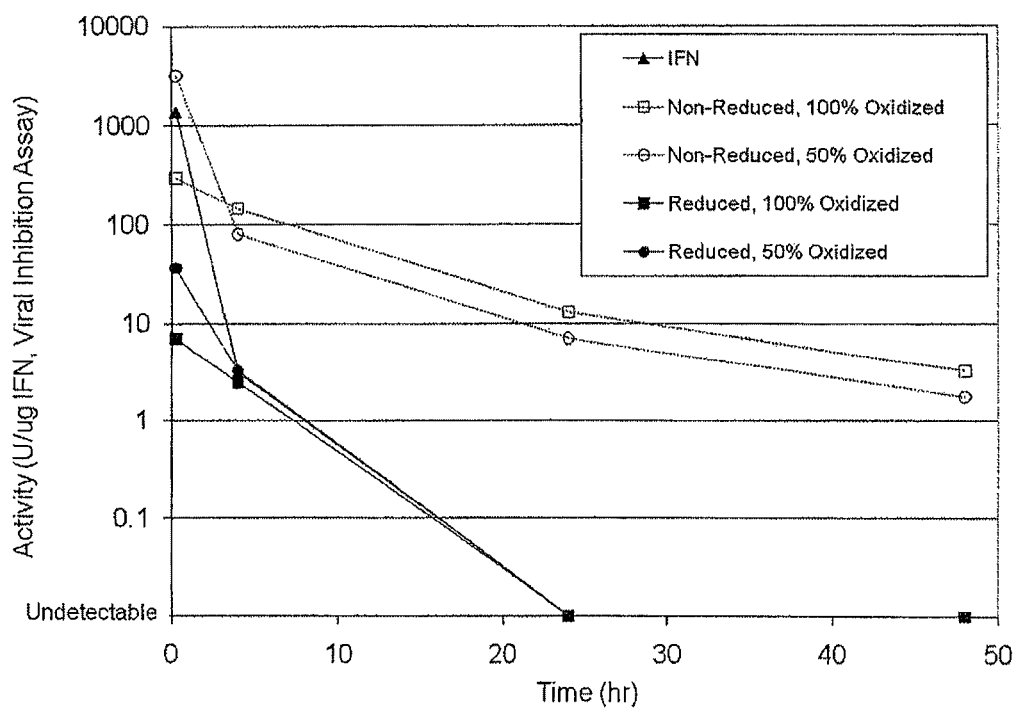
FIG. 2 is a graph of protein activity vs time (Ex vivo activity data for IFN).

All animals survived until terminal blood collection. Activity data are corrected for total IFN (microgram) injected. Negative control PBS group activities were below the limit of detection at all time points (~0.07 U/microgram). Positive control IFN group activity was 1,398 U/microgram at 15 min and decreased to 3 U/microgram by 4 hr, then to below the limit of detection (LOD) at 24 and 48 hr, indicating that free IFN is quickly cleared from circulation (Table 3, FIG. 2). IFN activity for both reduced conjugates (100% and 50% oxidized HES) was 7-37 U/microgram at 15 min, decreased to 2-3 U/microgram by 4 hr, then to below LOD at 24 and 48 hr. Both non-reduced conjugates had higher IFN activities at all time points compared to the reduced conjugates. The non-reduced 50% oxidized HES conjugate had higher 15 min activity than the 100% oxidized HES conjugate (3,201 vs 293 U/microgram), and both non-reduced conjugates had equal activities at later time points.

TABLE 3

IFN activity following test article administration in mice.

| | | IFN Activity (U/microgram) | | | |
|---|---|---|---|---|---|
| Group | Test Article | 15 min | 4 hr | 24 hr | 48 hr |
| 1 | Non-reduced 100% Oxidized HES | 293 | 147 | 13 | 3 |
| 2 | Reduced 100% Oxidized HES | 7 | 2 | <0.07 | <0.07 |
| 3 | Non-reduced 50% Oxidized HES | 3,201 | 80 | 7 | 2 |
| 4 | Reduced 50% Oxidized HES | 37 | 3 | <0.07 | <0.07 |
| 5 | IFN | 1,398 | 3 | <0.07 | <0.07 |
| 6 | PBS | <0.07 | <0.07 | <0.07 | <0.07 |
| 7 | Untreated control | NA | NA | NA | NA |

In Vivo Pharmacokinetics

Mice showed no adverse response to the HES-IFN compositions following administration. HES-IFN compositions had longer circulatory half-lives than unmodified IFN, as indicated by the longer duration of activity in the non-reduced compositions. Activity in the non-reduced composition groups was ~25-50× greater than for free IFN group at 4 hr, and at least 25-250× above the LOD from 24-48 hr, when the free IFN group showed no remaining activity. Non-reduced HES-IFN compositions had roughly 25-250-fold greater initial and sustained activity than reduced compositions. This is likely due to the slow dissociation and release of active IFN from the non-reduced compositions. A lower degree of HES oxidation correlated with a higher early activity for both the reduced and non-reduced compositions. In the case of the non-reduced compositions, this is likely due to more facile dissociation of IFN from the less-oxidized HES, which would have fewer aldehyde groups for linkage to the protein than the more-oxidized HES (see FIG. 2).

Example 13

General Procedure for In Vitro Characterization and Bioactivity

Non-reduced compositions containing <25% unmodified protein are considered suitable for bioactivity analysis. These compositions are selected for characterization of protein dissociation rate from the conjugate, and for bioactivity analysis. Non-reduced compositions and their reduced analogs are prepared at larger scale and purified by ultrafiltration. Compositions are incubated in either rodent plasma, PBS, or PBS containing albumin and representative plasma amines at 37° C. at concentrations simulating infusions of 0.1, 1 and 10% of animal blood volume. At 0, 2, 8, 24, 48 and 72 h, aliquots are removed and analyzed by SEC or PAGE to determine the degree of protein modification and molecular weight distribution (MWD) of the protein-containing components. Aliquots are also assayed for biological activity using established methods. All methods are corrected for potential interference from components of the compositions.

Example 13a

Demonstration of Releasability

HES-modified proteins were incubated with various amino acids, ammonium sulfate or albumin to demonstrate reversibility of attachment through transimination processes similar to those that would occur in vivo.

Figure 3:
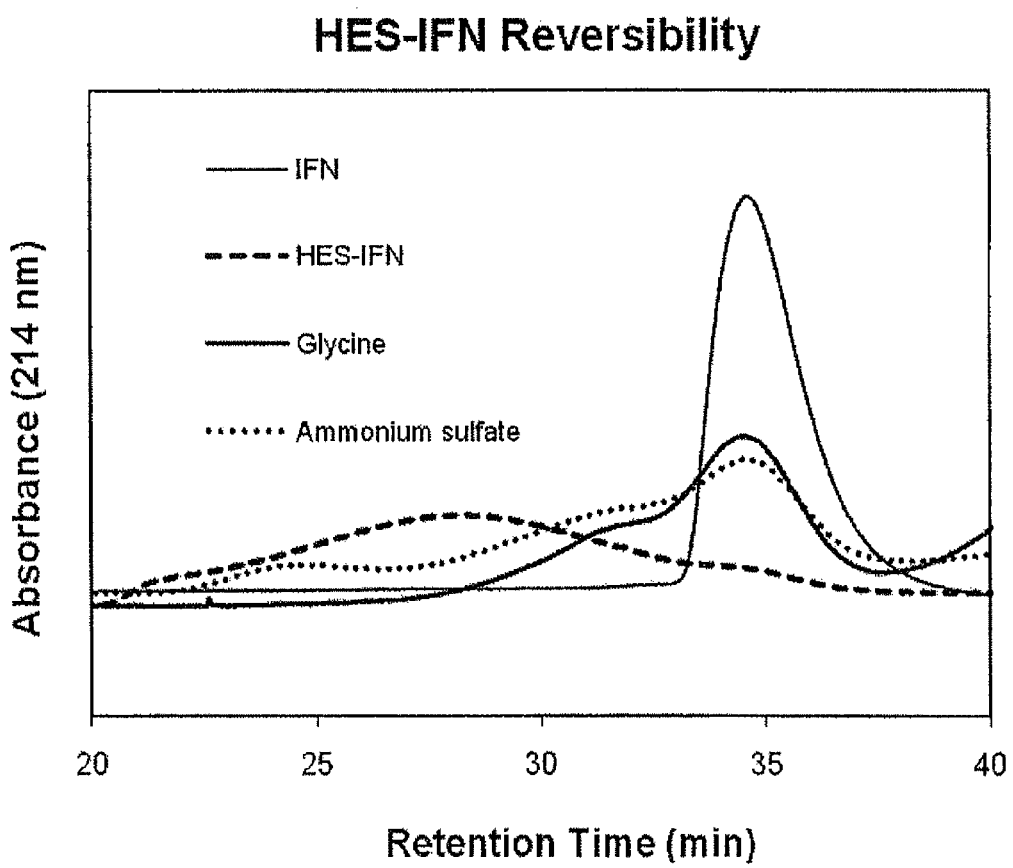
FIG. 3 is a HPLC trace showing HES-IFN reversibility.

FIG. 3 shows a HPLC trace of HES-IFN reversibility. The interferon (IFN, 35 min.) is modified with HES (200 kDa, 100% oxidized) to form HES-modified interferon (HES-IFN) and results in a broad, high molecular weight, earlier-eluting product (20-34 min). The peak corresponding to free interferon was re-formed in solution over 72 h with addition of glycine or ammonium sulfate, indicative of slow release of the protein from the HES carrier by transimination.

Figure 4:
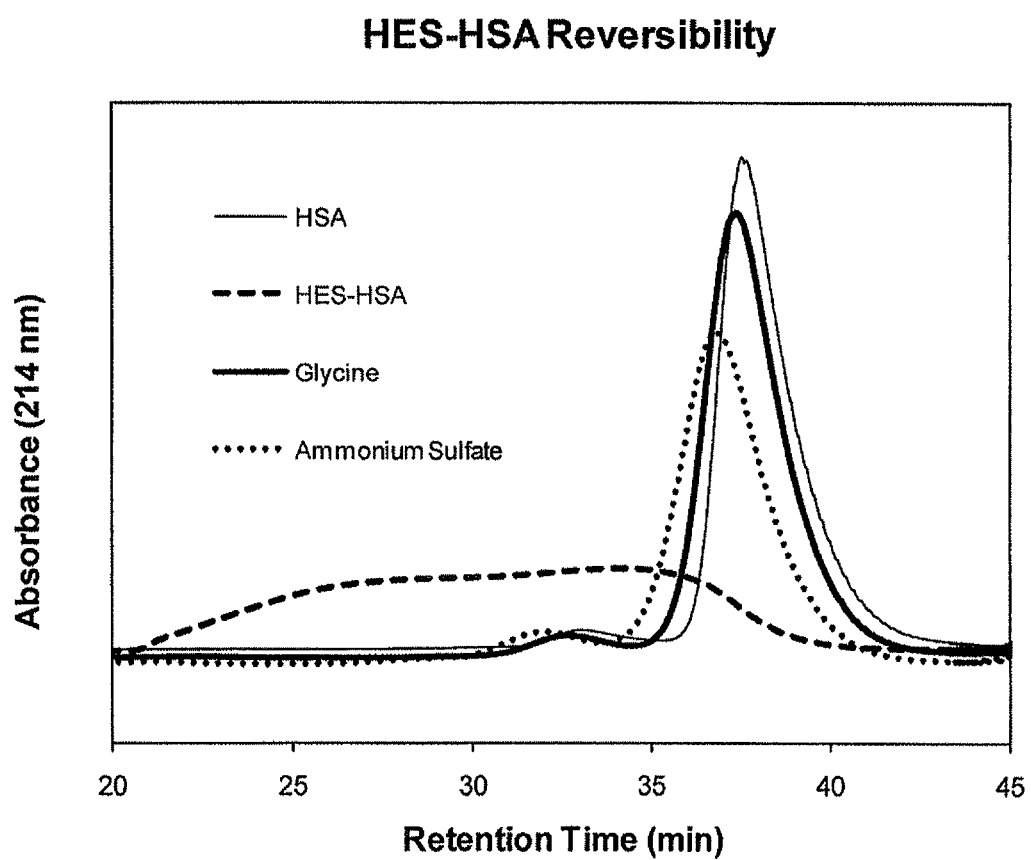
FIG. 4 is a HPLC trace showing HES-albumin reversibility.

FIG. 4 shows an HPLC trace of HES-albumin reversibility. The albumin (HSA, 38 min.) is modified with HES (200 kDa, 100% oxidized) to form HES-modified albumin (HES-HSA) and results in a broad, high molecular weight, earlier-eluting product (20-38 min). The peak corresponding to free albumin was re-formed in solution over 72 h with addition of glycine or ammonium sulfate, indicative of slow release of the protein from the HES carrier by transimination.

Example 14

General Procedure for In Vivo Characterization and Bioactivity

Non-reduced protein compositions containing <25% unmodified protein are considered suitable for in vitro and in vivo bioactivity studies. Non-reduced compositions and in some cases their reduced analogs are prepared at larger scale under sterile conditions and purified by ultrafiltration. Compositions are administered to suitable animal models intravenously. Unmodified protein and vehicle are administered in separate animal groups as controls. Blood samples are drawn and plasma prepared for quantification of protein and measurement of protein activity. The amount of protein is quantified by standard techniques. Activity is measured using an established protein activity assay.

Example 14a

Figure 5:
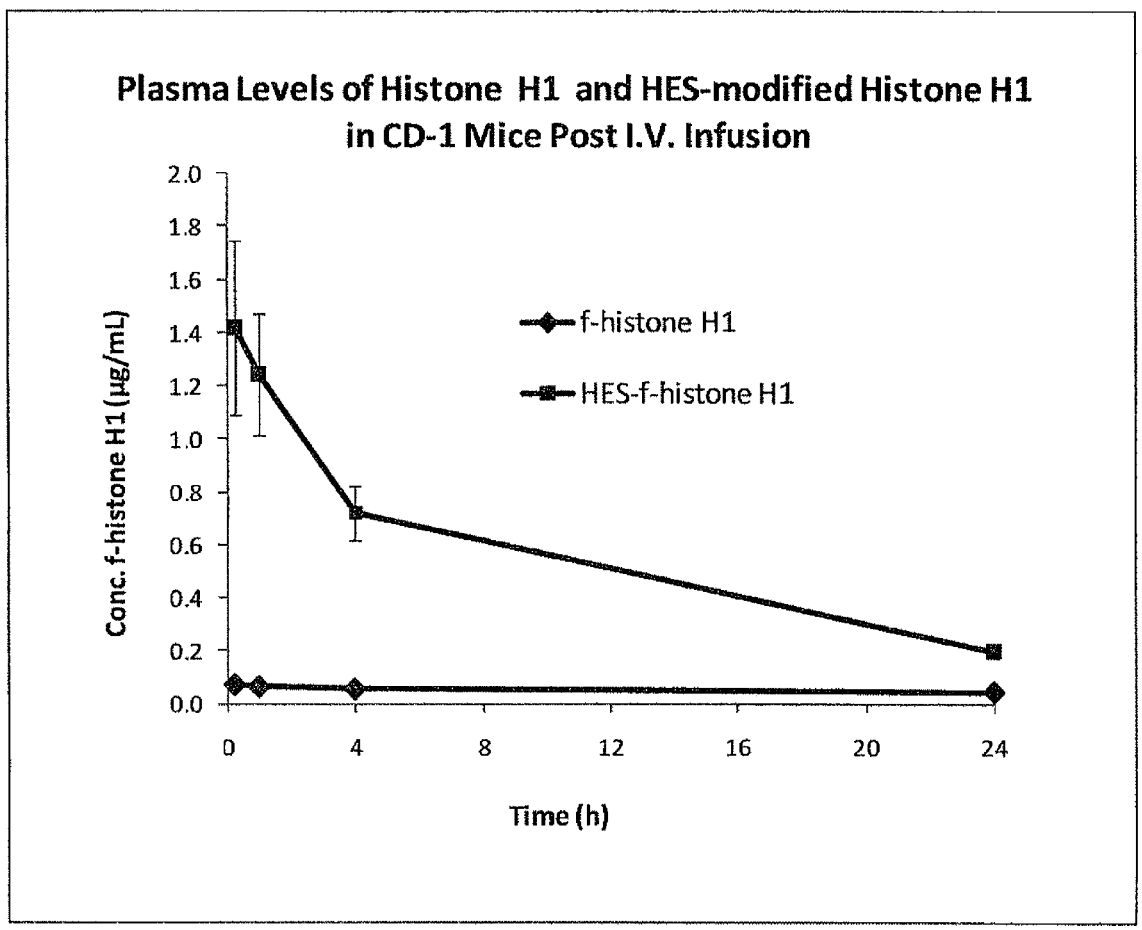
FIG. 5 is a graph showing the plasma levels of Histone H1 and HES-modified Histone H1 in CD-1 mice post iv. infusion.

In Vivo Detection of Alexa Fluor 488 Fluorescently Labelled Histone H1 as a Model Protein Fluorescently labelled Histone H1 (f-histone H1, from Invitrogen) was used as a model protein due to its small size (and therefore great potential to benefit from HES-modification with a resultant PK enhancement). IFN pharmacokinetics in Example 12 were based on measurements of IFN activity and not actual detection of IFN (HES-modification makes it inherently difficult to use traditional techniques such as ELISA and HPLC to detect the modified proteins in plasma due to the presence of other plasma proteins at a higher concentration that co-elute under the chromatography conditions). f-Histone H1 (2 Alexa Fluor 488 dyes per protein) was modified with oxiHES (200 kDa, 100% oxidized, 1:1 molar reaction ratio based on the WAMW of the HES, PBS pH 7.4, 37° C., 15 min., no purification). The formulation was diluted to 0.05 mg/mL with PBS, pH 7.4, and frozen until injection. The thawed solution in PBS (0.05 mg/mL) was dosed in CD-1 mice at 0.2 mg/kg using a 100 µL dose volume. 27 mice were terminated at specified time points (3 mice per time point, 4 time points: 15 min, 1, 4, and 24 h for HES-f-Histone H1 and f-Histone H1, plus three control mice receiving PBS) by exsanguination via cardiac puncture and the plasmas harvested. The plasmas were analyzed on a plate reader set to 485 nm and 530 nm absorption and emission wavelengths for Alexa Fluor 488 detection. Fluorescent values in plasma were converted to µg/mL of protein based on the specific fluorescence of the labeled protein in plasma determined previously. FIG. 5 shows the concentration curves. Non-HES-modified f-histone H1 showed a large prolongation in plasma compared to the unmodified protein and was barely detectable at any time point. HES-f-histone H1 remained detectable for the duration of the experiment (24 h).

Example 15

Polysaccharide-Enzyme Composition Preparation, Characterization and Activity

Preparation of Compositions

A range of compositions comprising an enzyme and an oxidized polysaccharide were prepared by similar methods and characterized. Enzymes used included L-asparaginase, uricase, deoxyribonuclease, superoxide dismutase, catalase and streptokinase.

Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable alternative buffer using a 10 kDa MWCO membrane and the concentrations adjusted to obtain compositions suitable for in vitro or in vivo evaluation.

In Vitro Characterization and Bioactivity

Non-reduced compositions containing <25% unmodified enzyme are considered suitable for bioactivity analysis. These compositions are selected for characterization of enzyme dissociation rate from the conjugate, and for enzymatic activity analysis. Non-reduced compositions and their reduced analogs are prepared at larger scale under sterile conditions and purified by ultrafiltration. Compositions are incubated in either rodent plasma, PBS, or PBS containing albumin and representative plasma amines at 37° C. at concentrations simulating infusions of 0.1, 1 and 10% of animal blood volume. At 0, 2, 8, 24, 48, 72 and 96 hr, aliquots are removed and analyzed by size exclusion chromatography to determine the degree of enzyme modification and molecular weight distribution (MWD) of the enzyme-containing components. Aliquots are also assayed for enzymatic activity using established methods. All methods are corrected for potential interference from components of the compositions.

In Vivo Characterization and Bioactivity

Non-reduced enzyme compositions containing <25% unmodified enzyme and showing an increase in free enzyme content and enzyme activity during in vitro incubation studies are considered suitable for in vivo bioactivity studies. Non-reduced compositions and their reduced analogs are prepared at larger scale under sterile conditions and purified by ultrafiltration. Compositions are administered to rodents intravenously, and in separate studies, sub-cutaneously (intravenously). Unmodified enzyme and vehicle are administered in separate animal groups as controls. Blood samples are drawn and plasma prepared for quantification of enzyme and measurement of enzyme activity. The amount of enzyme is quantified by either nephelometry or PAGE. Activity is measured using an established enzyme activity assay.

Example 15a

HES-Uricase

Preparation of Compositions

Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation.

Preparation of oxiHES-Uricase using 100% Oxidized 200 kDa HES

Uricase (from *Candida Utilis*, Worthington Biochemical) was made up to 10 mg/mL in WFI. 100 µL of the unease solution was mixed with 50 µL of 20× PBS pH 7.4 and 72 µL of 38.2 mg/mL 100% oxidized 200 kDa HES (prepared as described in example 1) and diluted with 778 µL of WFI to give 1 mL total reaction volume containing 1 mg/mL uricase. The ratio of HES to uricase was 1.75:1 based on the WAMW of 200 kDa for the oxiHES and 125 kDa for uricase. The mixture was gently agitated at 25° C. and monitored by HPLC injection at various time points (1, 2, 3, 6, 7, 24, 48, 72 h).

Biophysical Characterization

Figure 6:
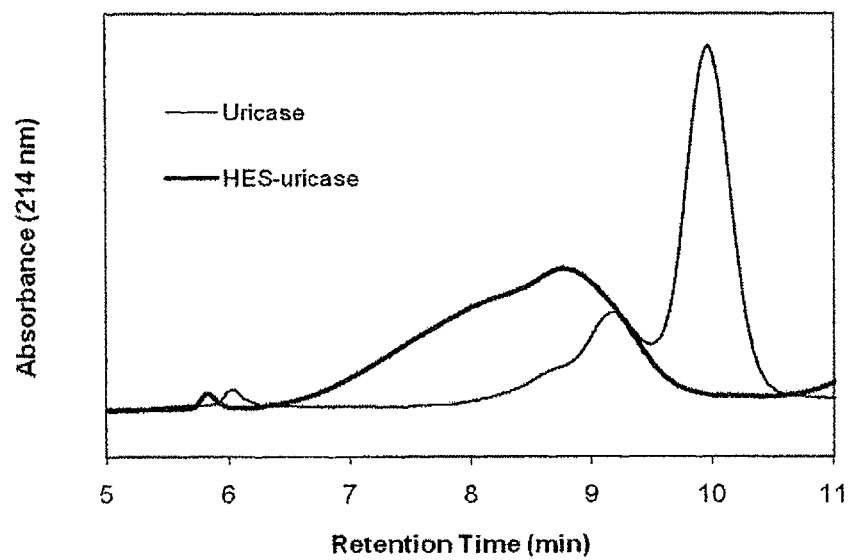
FIG. 6 is a HPLC trace showing HES-uricase (high molecular weight).

The composition contained very little unreacted uricase after only 1.5 h of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a faster-eluting higher molecular weight distribution of modified uricase ranging from 600 kDa down to 150 kDa. FIG. 6 shows the HPLC profile at selected time points of the reaction. This show that the uricase (10 min) when modified with HES (200 kDa, 100% oxidized) results in an earlier-eluting HES-modified product (HES-uricase, 7-9.5 min) with a broad and high molecular weight profile by SEC HPLC.

In Vitro Characterization and Bioactivity

The composition was assayed for activity after 2 h of reaction using an assay that measures the rate of depletion of uric acid by monitoring the decrease in 293 nm absorbance of the assay solution in which the protein is incubated with substrate uric acid in borate buffer pH 9. The activity of the HES-modified uricase had activity comparable to native uricase after 1.5 h of reaction and the activity is attributed to modified uricase since after this duration of reaction very little unreacted, native uricase was present. In the assay uricase and HES-uricase were assayed at the same concentration with equal dilution factors.

Preparation of oxiHES-Uricase using 25% Oxidized 200 kDa HES

Uricase (from *Candida Utilis*, Worthington Biochemical) was made up to 10 mg/mL in WFI. 100 µL of the uricase solution was mixed with 50 µL of 20× PBS pH 7.4 buffer and 4 µL of 69.9 mg/mL 100% oxidized 200 kDa HES (prepared as described in example 1) and diluted with 778 µL of WFI to give 1 mL total reaction volume containing 1 mg/mL uricase. The ratio of HES to uricase was 02:1 based on the WAMW of 200 kDa for the oxiHES and 125 kDa for uricase. The mixture was gently agitated at 25° C. and monitored by HPLC injection at various time points (1, 2, 3, 6, 7, 24, 48, 72 h).

Biophysical Characterization

Figure 8:
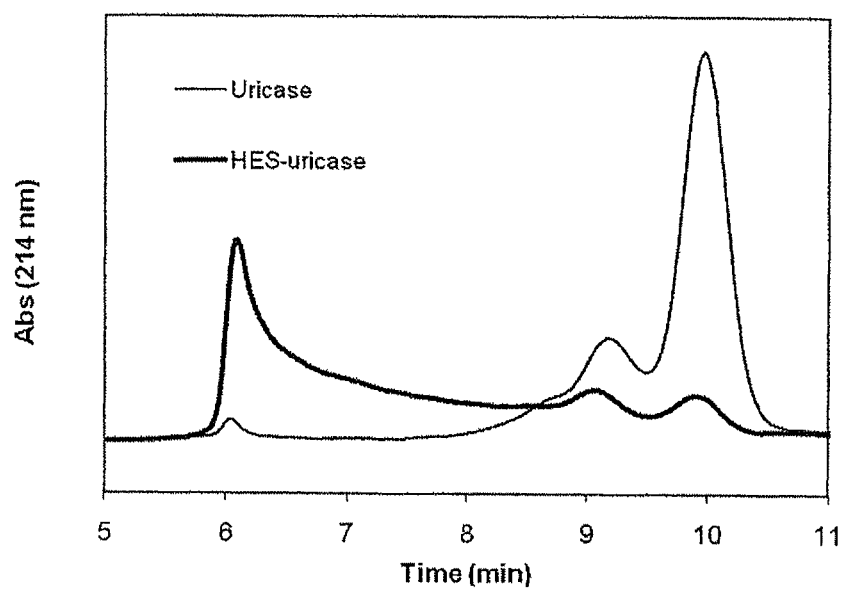
FIG. 8 is a HPLC trace showing HES-uricase (very high molecular weight).

The composition contained very little unreacted uricase after only 1.5 h of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a rapidly eluting, very high molecular weight distribution of modified uricase ranging from >600 kDa down to 200 kDa. FIG. 8 shows the HPLC profile at selected time points of the reaction. This shows that uricase (10 min) when modified with HES (200 kDa, 25% oxidized) results in an earlier-eluting HES-modified, very high-molecular weight polymerized product (HES-uricase, 6-8 min).

In Vitro Characterization and Bioactivity

Figure 7:
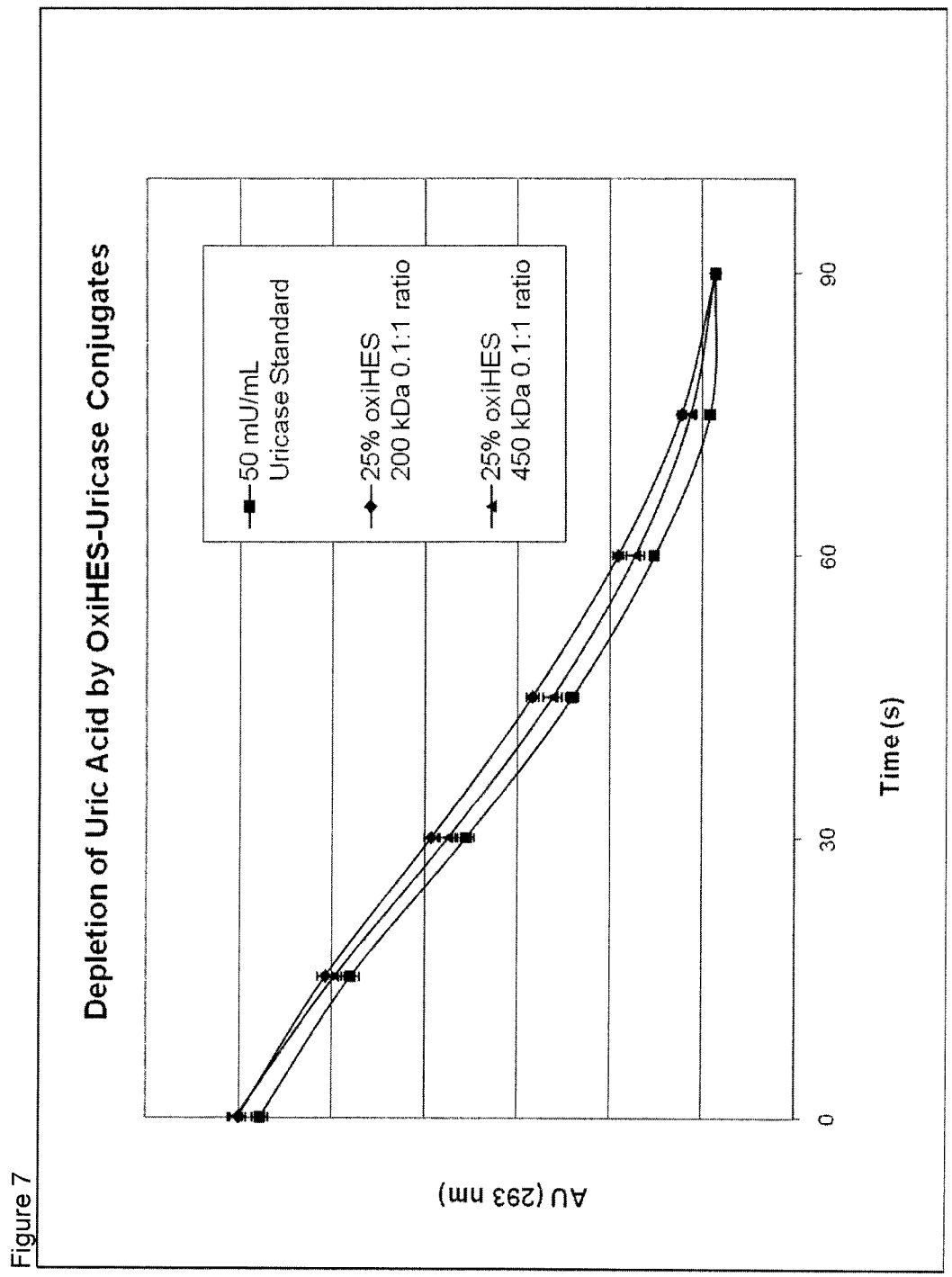
FIG. 7 is an activity plot of HES-uricase formulations (uric acid assay) using samples of selected conjugates diluted to 15.6 µg/mL (50 mU/mL) and then assayed to determine their rate of consumption of uric acid.
Figure 9:
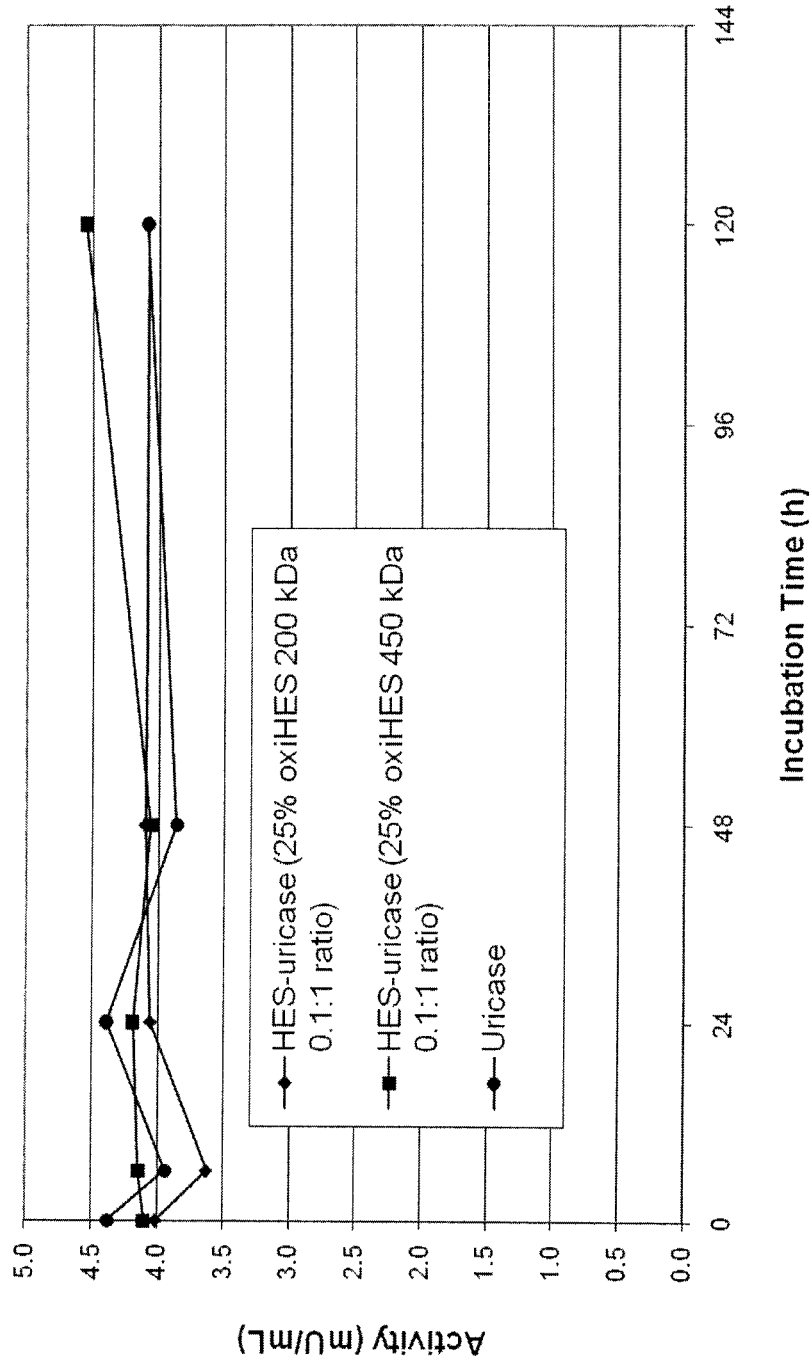
FIG. 9 is a graph of HES-uricase (very high molecular weight) plasma stability.

The composition was assayed for activity after 24 h of reaction using the uric acid assay described above. The activity of the HES-modified uricase had activity comparable to native uricase after 24 h of reaction and the activity is attributed to modified uricase since after this duration of reaction very little unreacted, native uricase was present. A similar conjugate made with 450 kDa oxiHES also had equivalent bioactivity to native uricase in the assay. In the assay uricase and HES-uricase were assayed at the same concentration with equal dilution factors. FIG. 7 shows the activity curves for the products and native uricase for comparison. Additionally, the product made from 200 kDa oxiHES was diluted into both CD-1 mouse and human plasma and incubated at 37° C. After 1, 4, and 24 h aliquots were withdrawn and assayed for activity using the Amplex Red assay (Invitrogen). Briefly, uricase and HES-uricase were incubated in plasma at a concentration of 100 mU/mL (~30 µg/mL based on the specific activity of 3200 mU/mg for the unease) and aliquots were diluted 20-fold with kit buffer for measurement in the assay. The conjugate had activity comparable to native uricase for all time points. FIG. 9 shows the results of the Amplex Red assay where selected conjugates were assayed for duration of activity in human plasma (the 100% OxiHES 200K plus uricase [which also appears in FIG. 6] is indicated by, ▲, the 25% OxiHES 200K plus unease [which also appears in FIG. 8] is indicated by, ♦ in FIG. 9). Samples maintained their activity for several days in vitro in human plasma.

In Vivo Characterization and Bioactivity

For comparison purposes, HES-uricase conjugate made from the reaction of 25% oxidized HES reacted with uricase in a 1:10 HES:protein ratio was treated with a 3.4-fold excess of dimethylamine borane complex per HES aldehyde to reduce all the Schiff Bases and reactive aldehydes in order to prepare a reduced, irreversible conjugate. This formulation was tested in CD-1 mice (Charles River Labs, St. Constant, QC, Canada) compared to the non-reduced conjugate as well as native unease. Both HES-uricase formulations, non-reduced and DMB-reduced, had equivalent activity to native uricase as determined using the uric acid assay. Mice (12 per group, 3 per time point) were dosed intravenously with 200 µL of 1 mg/mL (3,200 mU/mL) test article, resulting in an ~8 mg/kg dose of uricase (640 mU per mouse). Plasma samples were collected following terminal exsanguination via cardiac puncture. Uricase activity of the plasma samples were determined using the Amplex Red assay. Table 4 below shows the relative activities of the plasmas from mice injected with test articles compared to those from mice administered native uricase, indicating that non-reduced HES-uricase provided higher activity at later time points than did reduced HES-uricase and native uricase, the latter of which provided no detectable activity after 4 h.

TABLE 4

Plasma activities of CD-1 mice injected with uricase, HES-uricase, and DMB-reduced HES-uricase

| Test Article | Time (h) Post Injection | Uricase Activity Detected in Plasma (mU/mL) |
|---|---|---|
| Uricase | 8 | Not Detectable |
|  | 24 | Not Detectable |
| DMB-reduced HES-uricase | 8 | 62.7 ± 6.5 |
|  | 24 | Not Detectable |
| HES-uricase (Non-reduced) | 8 | 73.1 ± 25.1 |
|  | 24 | 44.8 ± 18.5 |

Example 15b

HES-Asparaginase

Preparation of Compositions

Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation.

For each oxidized HES preparation, the enzyme in WFI was combined with 1 M sodium phosphate pH 8 buffer and oxidized HES in WFI to achieve final oxiHES:asparaginase molar ratios of 0.2:1 and 1:1 and a final asparaginase concentrations of 5 mg/mL. (L-Asparaginase, from $E.\ Coli$, Prospec-Tany, Israel). Reaction mixtures were incubated at 37° C. At 5 min, 25 min, 1 h, 4 h, and 24 h, aliquots were removed and analyzed by size exclusion chromatography to determine the degree of enzyme modification and molecular weight distribution (MWD) of the asparaginase-containing mixtures. Samples were quenched with 100 mM sodium acetate pH 5 buffer and purified by dialysis against WFI.

Preparation of oxiHES-Asparaginase using 100% Oxidized 200 kDa HES

Asparaginase was made up to 10 mg/mL in WA. 150 μL of the asparaginase solution was mixed with 30 μL of 1 M sodium phosphate buffer, pH 8, and 50 μL of 38.2 mg/mL 100% oxidized 200 kDa HES (prepared as described in example 1) and diluted with 70 μL of WFI to give 0.3 mL total reaction volume containing 5 mg/mL asparaginase. The ratio of HES to asparaginase was 1:1 based on the WAMW of 200 kDa for the oxiHES and 140 kDa for asparaginase. The mixture was incubated at 37° C. and monitored by HPLC injection at various time points (5 min, 25 min, 1 h, 4 h, and 24 h).

Biophysical Characterization

Figure 10:
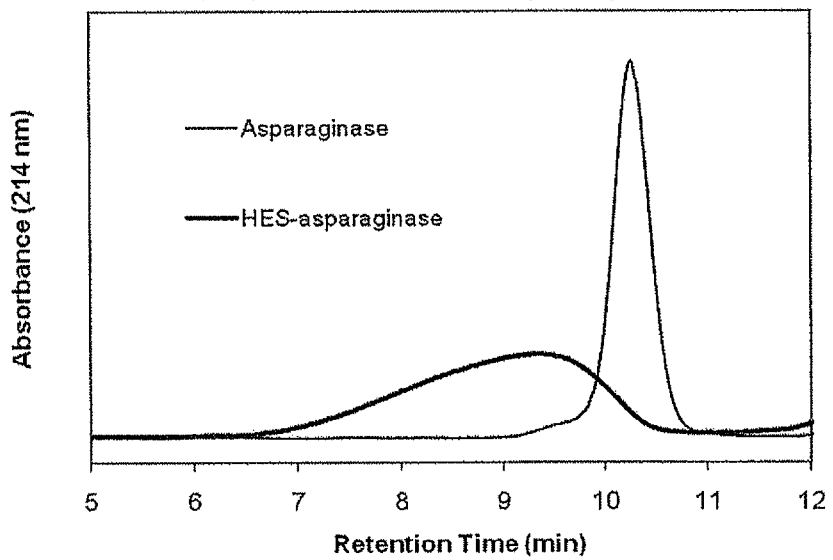
FIG. 10 is a HPLC trace showing HES-asparaginase.

The composition contained very little unreacted asparaginase after only 5 min. of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a faster-eluting, higher molecular weight, broad distribution of modified asparaginase ranging from 600 kDa down to 150 kDa. FIG. 10 shows the HPLC profile after 5 min. of reaction. This shows that asparaginase (10.2 min) when modified with HES (200 kDa, 100% oxidized) results in an earlier-eluting HES-modified product (HES-asparaginase, 7-10 min) with a broad and high molecular weight profile by SEC HPLC.

In vitro Characterization and Bioactivity

HES-asparaginase and asparaginase were assayed for activity using an assay based on quantification of ammonia released from asparagine upon incubation with the enzyme using Nessler's Reagent (Sigma Enzymatic Assay of asparaginase, EC 3.5.1.1). The specific activity of asparaginase and HES-asparaginase were comparable with minimal loss in specific activity.

In Vivo Characterization and Bioactivity

Figure 11:
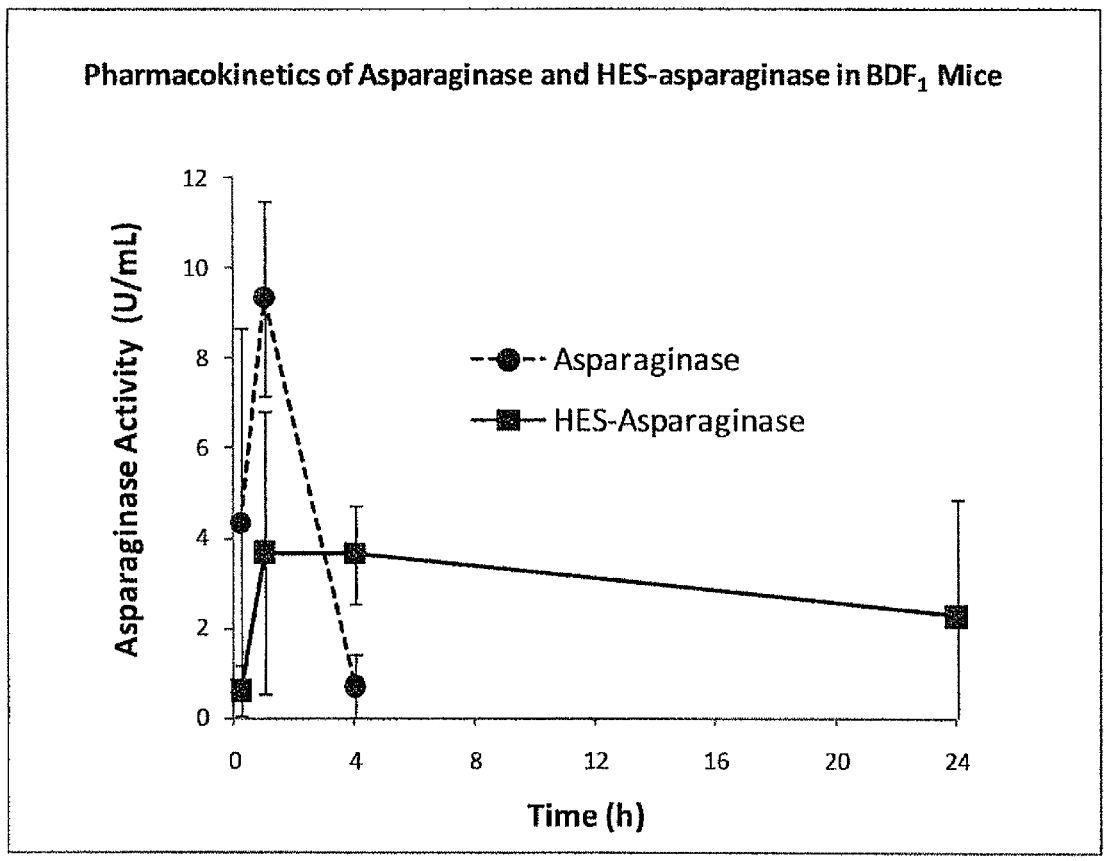
FIG. 11 is a graph showing the pharmacokinetics of asparaginase and HES-asparaginase in $BDF_1$ mice.

Plasma samples were assayed using the Sigma assay modified to measure plasma samples. FIG. 11 shows the plasma asparaginase activity levels for mice administered asparaginase compared to those administered HES-asparaginase. Study design: 27 mice (male $BDF_1$) were injected (intraperitoneal, i.p., 100 μL, 0.22 mg/mL asparaginase, ~5 IU/mouse) and terminated at specified time points (3 mice per time point, 4 time points: 15 min, 1, 4, and 24 h for HES-asparaginase and asparaginase, plus three control mice receiving PBS) by exsanguination via cardiac puncture and the plasmas harvested. The plasmas were assayed for asparaginase activity according to the Sigma assay using Nessler's Reagent. Unmodified asparaginase provided a peak in asparaginase activity by 1 h but provided no detectable activity above plasma baseline afterward. HES-asparaginase provided maximum activity after 1 h followed by detectable activity for the duration of the experiment (24 h), maintaining 62% of the peak activity at the 24 h time point.

Example 16

Polysaccharide-Enzyme Inhibitor Composition Preparation, Characterization and Activity Compositions of oxidized polysaccharides and a protein that is an enzyme inhibitor (alpha-1 antitrypsin) are prepared and characterized as described above in example 15 for polysaccharide-enzyme compositions. Activity refers to the bioactivity of the protein used. Assays for the detection and quantification of modified and unmodified protein, and assays for the activity of the protein, are selected from methods suitable to the protein used.

Example 16a

HES-Alpha-1 Antitrypsin (HES-A1AT)

Preparation of Compositions

Compositions are prepared as described in the Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation. For each oxidized HES preparation, human A1AT, in WFI was combined with 1 M sodium phosphate buffer (pH 6, 7, or 8) and oxidized HES (70, 200, and 450 kDa, 25-100% oxidized) in WFI to achieve final oxiHES:A1AT molar ratios of 02:1 and 1:1 and a final A1AT concentrations of 5 mg/mL. Reaction mixtures were incubated at 37° C. At 5 min, 25 min, 3 h, 6 h, and 24 h, aliquots were removed and analyzed by size exclusion chromatography to determine the degree of A1AT modification and molecular weight distribution (MWD) of the A1AT-containing mixtures. Samples were quenched with 100 mM sodium acetate pH 5 buffer and purified by dialysis against WFI.

Preparation of oxiHES-A1AT using 100% Oxidized 200 kDa HES

Human A1AT was made up to 10 mg/mL in WFI. 250 µL of the A1AT solution was mixed with 50 µL of 1 M sodium phosphate buffer, pH 8, and 200 µL of 38.2 mg/mL 100% oxidized 200 kDa HES (prepared as described in example 1) to give 0.5 mL total reaction volume containing 5 mg/mL A1AT. The ratio of HES to A1AT was 1:1 based on the WAMW of 200 kDa for the oxiHES and 52 kDa for A1AT. The mixture was incubated at 37° C. and monitored by HPLC injection at various time points (5 min, 25 min, 3 h, 6 h, and 24 h).

Biophysical Characterization

Figure 12:
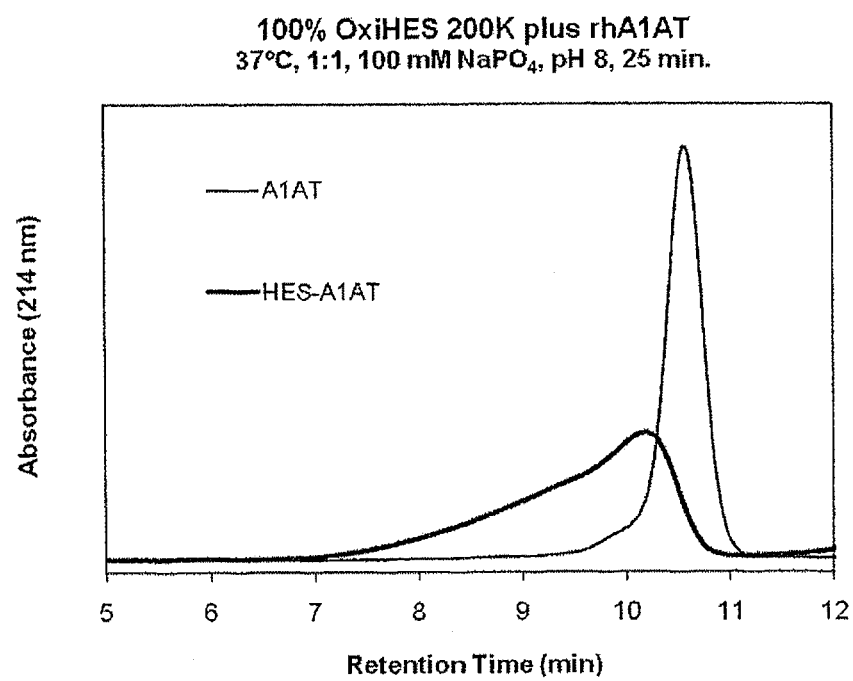
FIG. 12 is a HPLC trace showing HES-A1AT.

The composition contained very little unreacted A1AT after 25 min. of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a faster-eluting, higher molecular weight, broad distribution of modified A1AT ranging from 600 kDa down to 150 kDa. FIG. 12 shows the HPLC profile after 25 min. of reaction. This shows that alpha-1 Antitrypsin (A1AT, 10.6 min) when modified with HES (200 kDa, 100% oxidized) results in an earlier-eluting HES-modified product (HES-A1AT, 8-10.5 min) with a broad and high molecular weight profile by SEC HPLC.

In Vitro Characterization and Bioactivity

HES-A1AT and A1AT were assayed for activity using an assay based on impairment of neutrophil elastase to cleave a spectrophotometrically active substrate following binding to A1AT or HES-A1AT. The method is as described in Samis et. al. (Journal of Thrombosis and Haemostasis, 2, p 1535-44). Unmodified A1AT was measured to have an $IC_{50}$ of 0.02 µL, and HES-A1AT had an $IC_{50}$ of 0.03 µL when test articles were tested at 5.5 mg/mL based on A1AT protein content.

In Vivo Characterization and Bioactivity

Figure 13:
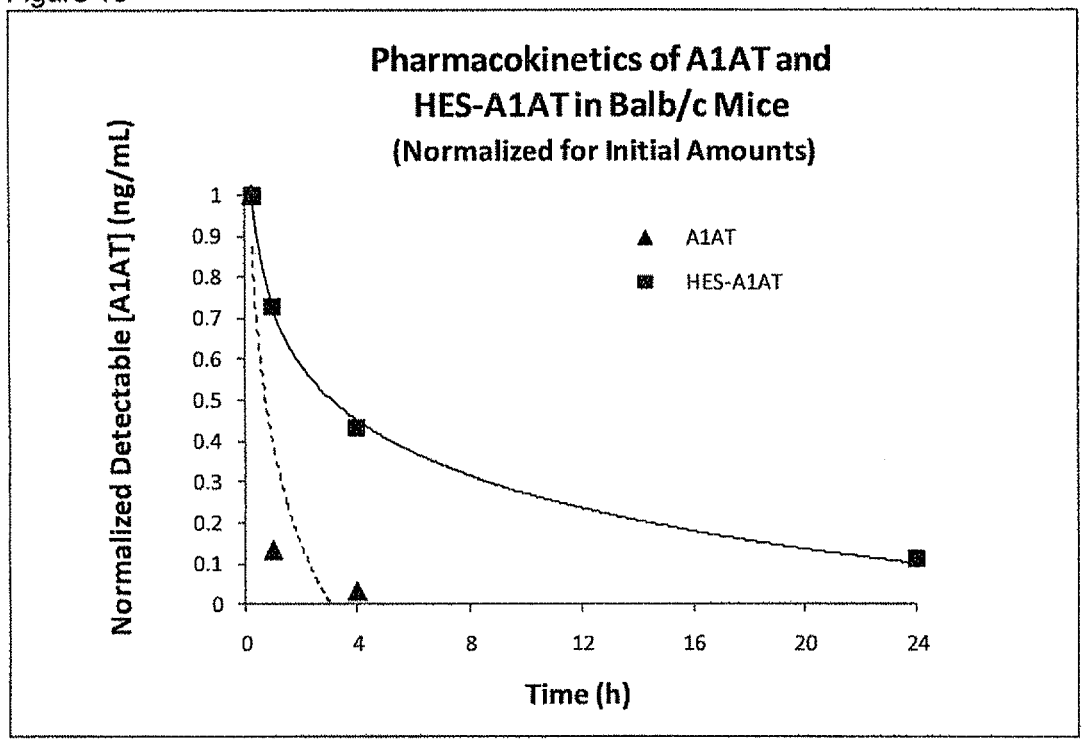
FIG. 13 is a graph showing the pharmacokinetics of rhA1AT and HES-A1AT in Balb/c mice.

A commercial ELISA detection kit was used to determine the effect of HES-modification on plasma circulation time of rhA1AT following administration. 27 mice (Balb/c, Charles River) were injected (i.v., 100 µL, 0.5 mg/mL A1AT) and terminated at specified time points (3 mice per time point, 4 time points: 15 min, 1, 4, and 24 h for HES-A1AT and A1AT, plus three control mice receiving PBS) by exsanguination via cardiac puncture and the plasmas harvested. The plasmas were analyzed using a commercially available ELISA (ICL Inc., catalog #E-80A1T). The binding affinity of the kit mAbs for the protein were reduced due to the nature of the HES-modification as expected (approximately 30-fold reduced binding). Even though the detection by ELISA was lower for HES-A1AT than for A1AT, the level of detectable A1AT in plasma did not decrease as rapidly over time in vivo for HES-A1AT as it did for A1AT, which decreased very quickly relative to the HES-modified conjugate, especially within the first 4 h (FIG. 13).

Example 17

Polysaccharide-Antibody Composition Preparation, Characterization and Activity

Compositions of oxidized polysaccharides and proteins that are antibodies (including anti-CD163) are prepared and characterized as described above for polysaccharide-enzyme compositions. Activity refers to the bioactivity of the protein used. Assays for the detection and quantification of modified and unmodified protein, and assays for the activity of the protein, are selected from methods suitable to the protein used.

Example 17a

HES-Anti-CD163 Monoclonal Antibody

Preparation of oxiHES-Anti-CD163 mAb using 100% Oxidized 200 kDa HES

Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation.

Murine hybridoma-derived anti-CD163 mAb (2E9A2) was made up to 10 mg/mL in WFI. 250 µL of the anti-CD163 mAb solution was mixed with 50 µL of 1 M sodium phosphate buffer, pH 8, 90 µL of 38.2 mg/mL 100% oxidized 200 kDa HES (prepared as described in example 1), and 110 µL of WFI diluent to give 0.5 mL total reaction volume containing 5 mg/mL anti-CD163 mAb. The ratio of HES to anti-CD163 mAb was 1:1 based on the WAMW of 200 kDa for the oxiHES and 150 kDa for the anti-CD163 mAb. The mixture was incubated at 37° C. and monitored by HPLC injection at various time points (5 min; 25 min, 1 h, 2 h, and 6 h of reaction).

Biophysical Characterization

Figure 14:
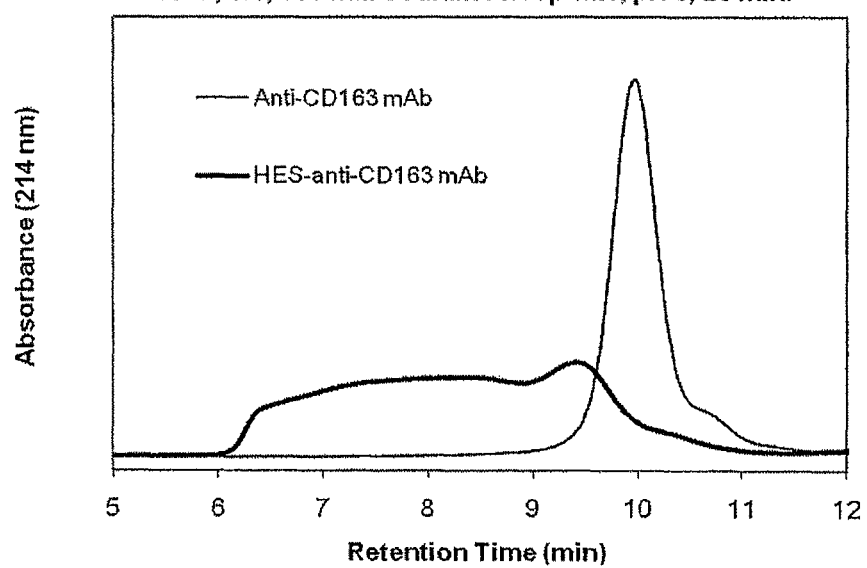
FIG. 14 is a HPLC trace showing HES-antiCD163mAb.

The composition contained predominantly modified antibody after only 5 min. of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a faster-eluting, higher molecular weight, broad distribution of modified anti-CD163 mAb ranging from 600 kDa down to 200 kDa. FIG. 14 shows the HPLC profile after 25 min. of reaction. This shows that anti-CD163 monoclonal antibody (Anti-CD163 mAb, 10 min) when modified with HES (200 kDa, 100% oxidized) results in an earlier-eluting HES-modified product (HES-anti-CD163 mAb, 6.2-10 min) with a broad and high molecular weight profile by SEC HPLC.

In Vitro Characterization and Bioactivity

Binding of the murine hybridoma-derived anti-CD163 antibody, 2E9A2, was determined using flow cytometry. Both wild-type (wt) HEK.293 cells and HEK.293 cells expressing the recombinant CD163 receptor were incubated first with the unlabeled 2E9A2 antibody preparations. Cells were then washed and further incubated with a goat-anti-mouse anti-IgG (GAM) antibody labelled with R-phycoerythrin (PE) for detection. After a final wash, cells were analyzed using a Beckman Coulter Epics XL flow cytometer to detect fluorescent cells.

Model In Vivo Binding Study

Figure 15A:
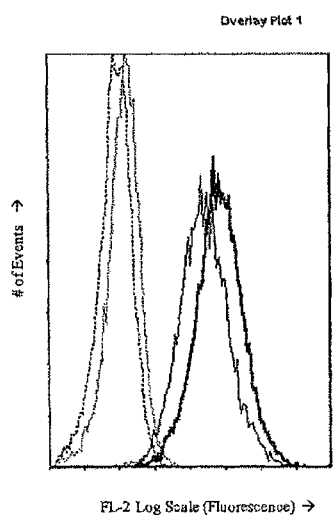
FIG. 15a is a plot showing the mean fluorescence intensity of CD163-expressing HEK 293 cells incubated with plasma containing antibody at 0 h and 24 h after incubation.
Figure 15B:
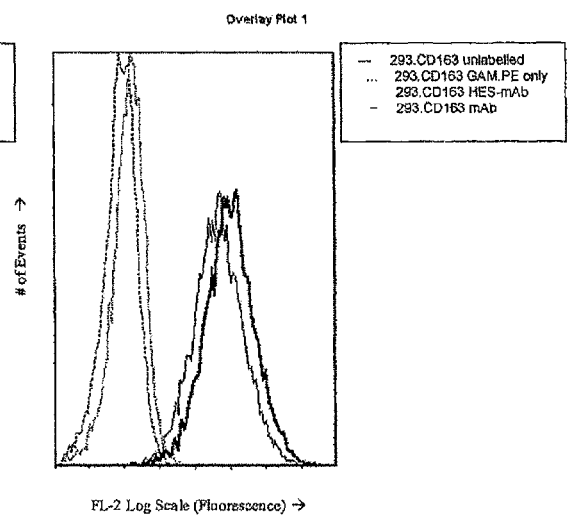
FIG. 15b is a plot showing the mean fluorescence intensity of CD163-expressing HEK 293 cells incubated with plasma containing HES-modified antibody at 0 h and 24 h after incubation.

In FIGS. 15a and 15b, the histograms show the distribution of fluorescence intensity of HEK.293.CD163$^+$ cells incubated with plasma containing either antibody and HES-modified antibody and GAM.PE. The signals for both are high and very similar (0 h of incubation) relative to negative controls (unlabeled cells and cells labelled only with GAM.PE secondary antibody) even though the degree of HES-modification for the HES-mAb is extensive. The degree of binding of the HES-mAb to the HEK.293.CD163+ cells following 24 h of incubation of the HES-mAb in plasma was not affected (24 h plasma samples containing the mAb and HES-mAb showed the same binding events or MFI). No binding of the antibody or HES-mAb was detected on the wt (non-CD163 expressing) HEK.293 cells. These data suggest that HES-modification does not affect the binding portion of the mAb and the conjugate or released mAb retains its ability to bind to its antigen (CD163 receptor) in plasma for 24 h.

Example 18

Polysaccharide-Cytokine Composition Preparation, Characterization and Activity

Compositions of oxidized polysaccharides and proteins that are cytokines (including G-CSF and insulin) are prepared and characterized as described above for polysaccharide-enzyme compositions. Activity refers to the bioactivity of the protein used. Assays for the detection and quantification of modified and unmodified protein, and assays for the activity of the protein, are selected from methods suitable to the protein used.

Example 18a

HES-G-CSF

Preparation of oxiHES-G-CSF using 100% Oxidized 200 kDa HES

Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation.

Recombinant human G-CSF (Prospec-Tany, Israel) formulated as 0.9 mg/mL in 10 mM sodium acetated buffer pH 4 was used as the stock solution. 250 µL of the G-CSF solution was mixed with 50 µL of 1 M sodium phosphate buffer, pH 8, 70 µL of 38.2 mg/mL 100% oxidized 200 kDa HES (prepared as described in example 1), and 130 µL of WFI diluent to give 0.5 mL total reaction volume containing 0.45 mg/mL G-CSF. The ratio of HES to G-CSF was 1:1 based on the WAMW of 200 kDa for the oxiHES and 18.8 kDa for the G-CSF. The mixture was incubated at 37° C. and monitored by HPLC injection at various time points (15 min, 45 min, 4 h, and 24 h of reaction.

Biophysical Characterization

Figure 16:
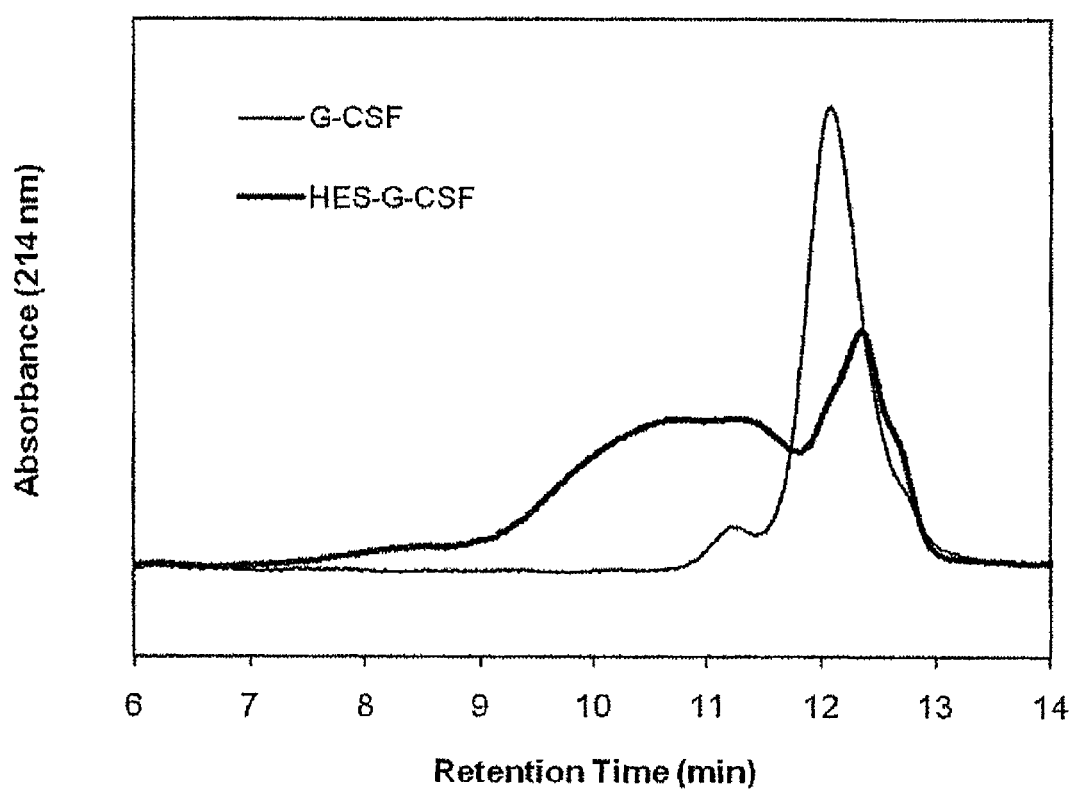
FIG. 16 is a HPLC trace showing HES-G-CSF.

The composition contained predominantly modified G-CSF after 45 min. of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a faster-eluting, higher molecular weight, broad distribution of modified G-CSF ranging from 600 kDa down to 200 kDa. FIG. 16 shows the HPLC profile after 25 min. of reaction. This shows that granulocyte-colony stimulating factor (G-CSF, 12 min) when modified with HES (200 kDa, 100% oxidized) results in an earlier-eluting HES-modified product (HES-G-CSF, 8-12 min) with a broad and high molecular weight profile by SEC HPLC. The peak at 12-13 min. is a low molecular weight oxiHES byproduct that partially co-elutes with unmodified G-CSF.

In Vitro Characterization and Bioactivity

HES-G-CSF and G-CSF were assayed for their proliferative effect on NFS-60 cells. The test articles were serially diluted (1:4) onto cells in a 96 well plate (20,100 cells/well) from 10,000 ng/mL down to 0.0002 ng/mL and their $ED_{50}$s were determined relative to internal standard G-CSF (commercial PeproTech G-CSF) by reading the O.D. (490 nm) 48 h following addition of Promega Substrate Cell Titer to the wells containing the cells and incubated test articles. G-CSF from Prospec-Tany had an $ED_{50}$ between 0.01 and 0.02 ng/mL and HES-G-CSF had a lower specific activity of between 0.1 and 0.15 ng/mL on the cells relative to G-CSF from Peprotech (0.03-0.04 ng/mL).

In Vivo Characterization and Bioactivity

In mice injected with HES-G-CSF, plasma G-CSF levels after 15 min. were found to be 4-fold higher than the G-CSF levels of mice injected with G-CSF after 15 min. G-CSF levels were quantified using the activity assay described above and correcting for the difference in specific activities.

Example 18b

HES-Insulin

Preparation of oxiHES-insulin using 100% oxidized 200 kDa HES Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation. Recombinant human insulin (250 µL, Sigma-Aldrich, made up to 1 mg/mL in water) was mixed with 50 µL of 1 M sodium phosphate buffer, pH 8, 113 µL of 67 mg/mL 100% oxidized 200 kDa HES (prepared as described in example 1), and 87 µL of WFI diluent to give 0.5 mL total reaction volume containing 0.5 mg/mL insulin. The ratio of HES to insulin was 1:1 based on the WAMW of 200 kDa for the oxiHES and 6 kDa for the insulin. The mixture was incubated at 37° C. and monitored by HPLC injection at various time points (5 min, 25 min, 1 h, 4 h, and 24 h of reaction. Insulin made up to 0.5 mg/mL without the addition of oxiHES, i.e. water substituted at the same volume, was not soluble, whereas the insulin conjugate was.

Biophysical Characterization

Figure 17:
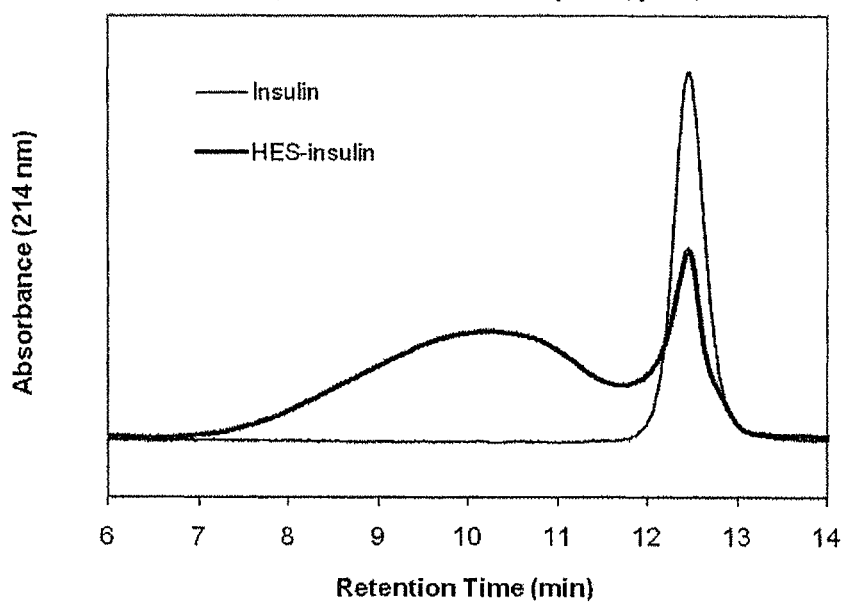
FIG. 17 is a HPLC trace showing HES-insulin.

The composition contained predominantly modified insulin after 5 min. of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a faster-eluting, higher molecular weight, broad distribution of modified insulin ranging from 600 kDa down to 100 kDa. FIG. 17 shows the HPLC profile after 5 min. of reaction. This shows that insulin (12.5 min) when modified with HES (200 kDa, 100% oxidized) results in an earlier-eluting HES-modified product (HES-insulin, 7.5-12 min) with a broad and high molecular weight profile by SEC HPLC. The peak at 12-13 min. is a low molecular weight oxiHES byproduct that co-elutes with unmodified insulin. This can be removed by dialysis.

In Vitro Characterization and Bioactivity

HES-insulin and insulin were assayed for their proliferative effect on MCF-7 cells. The test articles were serially diluted (1:5) onto cells (20,000 cells/mL, 100 µL) in a 96 well plate from 5000 ng/mL to 0.001 ng/mL and their $ED_{50}$s were determined relative to internal standard IGF-1 (commercial PeproTech standard) by reading the O.D. (490 nm) 92 h following addition of Promega Substrate Cell Titer to the wells containing the cells and incubated test articles. Insulin from Sigma had an $ED_{50}$ between 0.12 and 0.16 ng/mL and HES-insulin had a lower specific activity of between 7.3 and 11 ng/mL on the cells relative to human IGF-1 from Peprotech (0.11-0.17 ng/mL).

Example 19

Polysaccharide-Clotting Factor Composition Preparation, Characterization and Activity Compositions of oxidized polysaccharides and proteins that are clotting factors (including streptokinase and Factor VIII) are prepared and characterized as described above for polysaccharide-enzyme compositions. Activity refers to the bioactivity of the protein used. Assays for the detection and quantification of modified and unmodified protein, and assays for the activity of the protein, are selected from methods suitable to the protein used.

Example 19a

HES-Streptokinase

Preparation of oxiHES-Streptokinase using 100% Oxidized 200 kDa HES

Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation. Recombinant human streptokinase (Prospec-Tany, Israel) was made up to 20 mg/mL in water and dialyzed extensively against PBS. The stock solution also contained 14 mg/mL human serum albumin (HAS). 15 µL of the streptokinase stock solution containing HSA was mixed with 30 µL of 1 M sodium phosphate buffer, pH 8, 147 µL of 43.4 mg/mL 100% oxidized 200 kDa HES (prepared as described in example 1), and 108 µL of WFI diluent to give 0.3 mL total reaction volume containing 5 mg/mL streptokinase. The ratio of HES to streptokinase was 1:1 based on the WAMW of 200 kDa for the oxiHES and 47 kDa for the streptokinase. The mixture was incubated at 37° C. and monitored by HPLC injection at various time points (15 min, 45 min, 4 h, and 24 h of reaction.

Biophysical Characterization

Figure 18:
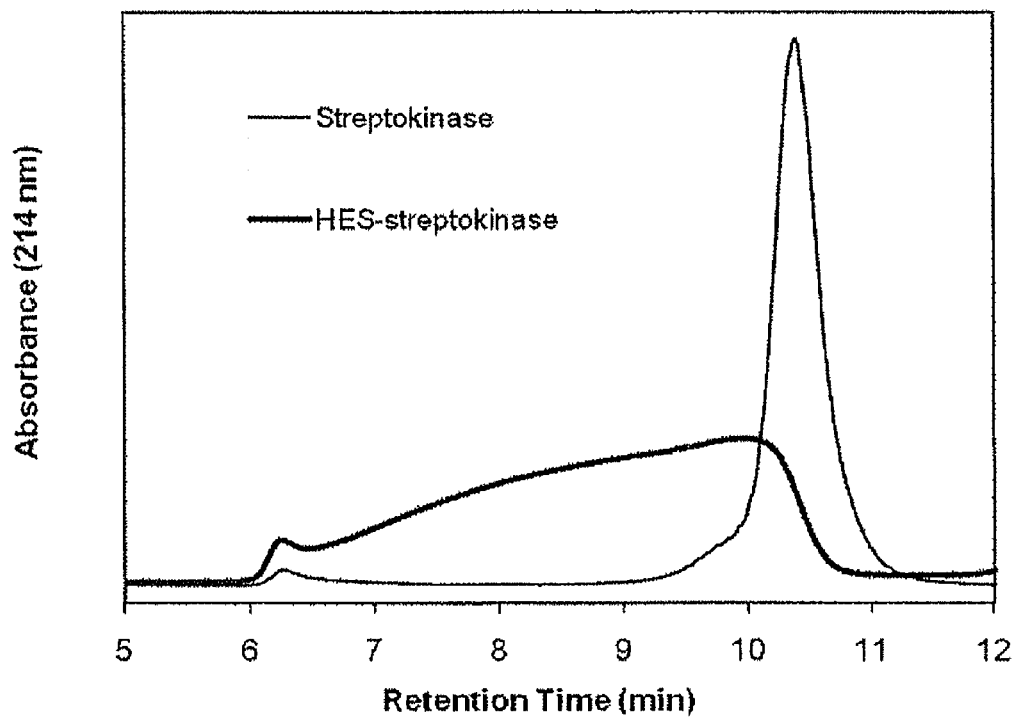
FIG. 18 is a HPLC trace showing HES-streptokinase.

The composition contained predominantly modified streptokinase and albumin after 45 min. of reaction time as analyzed by size-exclusion HPLC (Phenomenex BioSep SEC S4000 column, PBS pH 7.4 buffer mobile phase, 1 mL/min, Absorbance measured at 214 and 280 nm). The product appeared as a faster-eluting, higher molecular weight, broad distribution of modified streptokinase and albumin ranging from 600 kDa down to 200 kDa. FIG. 18 shows the HPLC profile after 25 min. of reaction. This shows that streptokinase (10.5 min) when modified with HES (200 kDa, 100% oxidized) results in an earlier-eluting HES-modified product (HES-streptokinase, 6-10.5 min) with a broad and high molecular weight profile by SEC HPLC. The product actually is a mixture of streptokinase, HSA and oxiHES, since the ratio of HSA to streptokinase in the stock solution was approximately 0.7:1, and there is no peak detectable above the trace of the HES-product peak distribution corresponding to where albumin would elute if present in an unconjugated form at that concentration.

Example 19b

HES-Factor VIII

Preparation of oxiHES-Factor VIII Using 100% Oxidized 200 kDa HES

Compositions are prepared as described in Example 4 above. At various time points, aliquots are removed and analyzed by size exclusion chromatography to determine the degree of enzyme modification and molecular weight distribution (MWD) of the enzyme-containing components. Samples are also removed and dialyzed if necessary against PBS or suitable buffer using a 10 kDa MWCO membrane and the concentrations adjusted to obtain compositions suitable for in vitro or in vivo evaluation. Recombinant factor VIII (Prospec-Tany, Israel) was dissolved in PBS to make a stock solution of 1 mg/mL. After dialysis the concentration was determined to be 0.6 mg/mL due to swelling and dilution. 500 µL of the factor VIII solution was mixed with 100 µL of 1 M sodium phosphate buffer, pH 8, 238 µL of 38.2 mg/mL 100% oxidized 200 kDa HES (prepared as described in example 1), and 162 µL of WFI diluent to give 1 mL total reaction volume containing 0.3 mg/mL factor VIII. The ratio of HES to factor VIII was 44:1 based on the WAMW of 200 kDa for the oxiHES and 18.8 kDa for the factor VIII. The mixture was incubated at 37° C. and monitored by HPLC injection at various time points (15 min, 45 min, 4 h, and 24 h of reaction.

Biophysical Characterization

Figure 19:
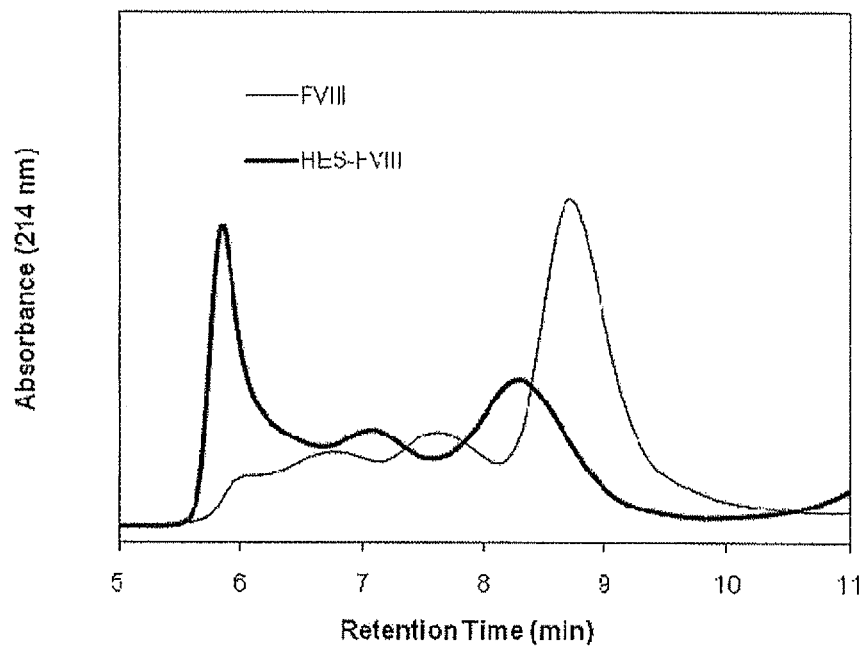
FIG. 19 is a HPLC trace showing HES-Factor VIII.

The composition contained predominantly modified factor VIII after 45 min. of reaction time as analyzed by size-exclusion HPLC (Phenomenex BioSep SEC 54000 column, PBS pH 7.4 buffer mobile phase, 1 mL/min, Absorbance measured at 214 and 280 nm). The product appeared as a faster-eluting, higher molecular weight, broad distribution of modified factor VIII ranging from 600 kDa down to 200 kDa. FIG. 19 shows the HPLC profile after 25 min. of reaction. This shows that factor VIII (FVIII, primarily at 8.9 min) when modified with HES (200 kDa, 100% oxidized) results in an earlier-eluting HES-modified product with primarily a sharp, very high molecular weight peak (6 min) as well as some broad and high molecular weight peaks (between 6.5 and 9 min) when analyzed by SEC HPLC.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention, which are obvious to those skilled in the relevant fields, are intended to be within the scope of the following claims.

The invention claimed is:

1. A method of preparing an oxidized polysaccharide-protein composition comprising the steps of:
 (a) oxidizing a polysaccharide with an alkali metal periodate compound to form an oxidized polysaccharide where less than 20% of the oxidized units are comprised of alpha-hydroxy aldehyde units;
(b) reacting the oxidized polysaccharide with a protein in the absence of a reducing agent to form a composition comprising an oxidized polysaccharide-protein conjugate,
(c) subjecting the oxidized polysaccharide-protein conjugate to dialysis;
(d) subjecting the dialyzed polysaccharide-protein conjugate to sterile filtration to allow for administration to a human or animal;
the oxidized polysaccharide and the protein being conjugated via one or more imine bonds which are not subjected to reduction;
the oxidized polysaccharide-protein composition being soluble in aqueous solvent;
the composition being capable of releasing the protein.

2. A method according to claim 1, wherein the polysaccharide is selected from cellulose, pectin, starch and hydroxyhydrocarbyl derivatives thereof.

3. A method according to claim 1, wherein the polysaccharide is selected from cellulose, pectin, starch, hydroxyalkyl cellulose and hydroxyalkyl starch.

4. A method according to claim 1, wherein the polysaccharide is hydroxyethyl starch.

5. A method according to claim 1, wherein the degree of oxidation of the oxidized polysaccharide is from 1 to 100%.

6. A method according to claim 1, wherein the weight average molecular weight of the polysaccharide is from 1 to 2000 kDa.

7. A method according to claim 1, wherein the ratio of oxidized polysaccharide to protein is from 0.1:1 to 20:1.

8. A method according to claim 1, wherein the oxidized polysaccharide is reacted with a protein in step (b) in the presence of at least one further protein such that the oxidized polysaccharide-protein composition comprises more than one protein and each protein is conjugated to the oxidized polysaccharide via one or more imine bonds.

9. A method according to claim 1, wherein the or each protein is selected from antibodies, cytokines, enzymes, growth factors and regulatory proteins.

10. A method according to claim 1, wherein the or each protein is selected from erythropoietin (EPO), granulocyte-colony stimulating factor (G-CSF), uricase, beta-glucocerebrosidase, alpha-galactosidase, C-1 inhibitor, streptokinase, DNAseI, alpha-1 antitrypsin, asparaginase, arginine deiminase, Factor IX, Factor VIIa, Factor VIII, Factor IIa (thrombin), anti-TNF-alpha antibody, tissue plasminogen activator, human growth hormone, superoxide dismutase, catalase, CD163 antibody, anti-VEGF, anti-thrombin antibody, anti-CD20 antibody, anti-IgG1 antibody, anti-HER2 antibody, anti-CD33 antibody, anti-IgG2a antibody, anti-EGFR antibody, histone, interferon, insulin, albumin and mixtures thereof.

11. A method according to claim 1, wherein the oxidized polysaccharide-protein conjugate is less than 0.1 µm in size.

12. A method according to claim 1, wherein the protein has a weight average molecular weight of greater than about 1 kDa.

13. A method according to claim 1, wherein the oxidized polysaccharide is reacted with a protein in step (b) in the absence of a molecular crowding agent.

14. A method according to claim 1, wherein the oxidized polysaccharide-protein composition further comprises non-conjugated protein.

15. A method of reversibly conjugating a protein to an oxidized polysaccharide comprising the steps of preparing an oxidized polysaccharide-protein composition according to claim 1, and dissolving the oxidized polysaccharide-protein composition in a solvent.

16. A method according to claim 1, wherein the polysaccharide has less than 15% 1,2,3-triol content.

17. A method according to claim 1 wherein the polysaccharide has less than 5% 1,2,3-triol content.

18. A method according to claim 1 wherein the polysaccharide has less than 1% 1,2,3-triol content.

19. A method according to claim 1, wherein the ratio of oxidized polysaccharide to protein is 1:1 molar equivalents of polysaccharide relative to protein.

20. A method according to claim 1, wherein the ratio of oxidized polysaccharide to protein is 0.1:1 molar equivalents of polysaccharide relative to protein.

21. A method according to claim 1, wherein the ratio of oxidized polysaccharide to protein is 10:1 molar equivalents of polysaccharide relative to protein.

22. A method according to claim 1, wherein the degree of oxidation of the oxidized polysaccharide is 100%.

23. A method according to claim 1, wherein step (b) is carried out at a pH of 6-8.

24. A method according to claim 1, wherein step (a) is carried out at a temperature of less than 20° C. and step (b) is carried out at a temperature of at least 5° C.

* * * * *